(12) United States Patent
Bjerregaard et al.

(10) Patent No.: US 11,622,996 B2
(45) Date of Patent: Apr. 11, 2023

(54) SOLID COMPOSITIONS COMPRISING A GLP-1 AGONIST AND A SALT OF N-(8-(2-HYDROXYBENZOYL)AMINO) CAPRYLIC ACID

(71) Applicant: Novo Nordisk A/S, Bagsvaerd (DK)

(72) Inventors: Simon Bjerregaard, Hilleroed (DK); Ulrik Lytt Rahbek, Charlottenlund (DK); Philip Jonas Sassene, Copenhagen V (DK); Jorrit Jeroen Water, Frederiksberg (DK); Andreas Vegge, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 17/053,511

(22) PCT Filed: May 6, 2019

(86) PCT No.: PCT/EP2019/061502
§ 371 (c)(1),
(2) Date: Nov. 6, 2020

(87) PCT Pub. No.: WO2019/215063
PCT Pub. Date: Nov. 14, 2019

(65) Prior Publication Data
US 2021/0236601 A1    Aug. 5, 2021

(30) Foreign Application Priority Data

May 7, 2018   (EP) .................................... 18171046

(51) Int. Cl.
| | | |
|---|---|---|
| A61K 38/26 | (2006.01) | |
| A61K 9/00 | (2006.01) | |
| A61K 47/10 | (2017.01) | |
| A61K 47/14 | (2017.01) | |
| A61K 47/18 | (2017.01) | |
| A61K 47/22 | (2006.01) | |

(52) U.S. Cl.
CPC ............ *A61K 38/26* (2013.01); *A61K 9/0053* (2013.01); *A61K 47/10* (2013.01); *A61K 47/14* (2013.01); *A61K 47/183* (2013.01); *A61K 47/22* (2013.01)

(58) Field of Classification Search
CPC ....... A61K 38/26; A61K 9/0053; A61K 47/10
See application file for complete search history.

(56) References Cited

U.S. PATENT DOCUMENTS

| | | | |
|---|---|---|---|
| 5,382,574 | A | 1/1995 | Joergensen |
| 6,440,930 | B1 | 8/2002 | Rinella, Jr. |
| 9,278,123 | B2 | 3/2016 | Sauerberg et al. |
| 10,028,910 | B2 | 7/2018 | Brunner-Schwarz et al. |
| 10,029,011 | B2 | 7/2018 | Hagendorf et al. |
| 11,167,014 | B2 | 11/2021 | Vegge et al. |
| 2003/0050237 | A1 | 3/2003 | Kim et al. |
| 2003/0069182 | A1 | 4/2003 | Rinella |
| 2006/0286129 | A1 | 12/2006 | Sarubbi |
| 2007/0128193 | A1 | 6/2007 | O'Neil et al. |
| 2008/0026070 | A1 | 1/2008 | Bonnet-Gonnet |
| 2009/0186819 | A1 | 7/2009 | Carrier et al. |
| 2010/0080829 | A1 | 4/2010 | Dulieu et al. |
| 2010/0144621 | A1 | 6/2010 | Kim et al. |
| 2010/0323065 | A1 | 12/2010 | Smith |
| 2014/0100156 | A1 | 4/2014 | Haack et al. |
| 2015/0157619 | A1 | 6/2015 | Kiyoshima et al. |
| 2015/0202296 | A1 | 7/2015 | Khan et al. |
| 2015/0232527 | A1 | 8/2015 | Gong et al. |
| 2016/0151462 | A1 | 6/2016 | Sauerberg et al. |
| 2016/0235855 | A1 | 8/2016 | Xiong et al. |
| 2019/0309040 | A1 | 10/2019 | Thennati et al. |
| 2020/0000728 | A1 | 1/2020 | Pedersen et al. |

FOREIGN PATENT DOCUMENTS

| | | |
|---|---|---|
| CL | 2012001232 A1 | 10/2012 |
| CL | 2012001233 A1 | 10/2012 |
| CL | 2019003402 A1 | 3/2020 |
| CL | 2020001899 A1 | 10/2020 |
| CL | 2020002574 A1 | 6/2021 |
| JP | H05502234 A | 4/1993 |
| JP | 2002-524514 | 8/2002 |
| JP | 2009274983 A | 11/2009 |
| RU | 2487647 C1 | 7/2013 |
| WO | 9620005 A1 | 7/1996 |
| WO | 97/07814 A1 | 3/1997 |
| WO | 0015224 A1 | 3/2000 |
| WO | 00/62759 A1 | 10/2000 |
| WO | 02/098348 A2 | 12/2002 |
| WO | 2005/097175 A2 | 10/2005 |
| WO | 2005107773 A2 | 11/2005 |
| WO | 2006014287 A1 | 2/2006 |
| WO | 2006068910 A1 | 6/2006 |
| WO | 2006084164 A2 | 8/2006 |

(Continued)

OTHER PUBLICATIONS

Dhapte et al., "Advances in hydrotropic solutions: An updated review" St. Petersburg Polytechnical University Journal: Physics and Mathematics, 2015, vol. 1, No. 4, pp. 424-435.
Steinert et al., "Oral Administration of Glucagon-Like Peptide 1 or Peptide YY 3-36 Affects Food Intake in Healthy Male Subjects," Am J Clin Nutr, Oct. 2010, vol. 92, pp. 810-817.

(Continued)

*Primary Examiner* — Gyan Chandra

(74) *Attorney, Agent, or Firm* — Leon Y. Lum

(57) ABSTRACT

The invention relates to pharmaceutical compositions comprising a GLP-1 agonist and a salt of N-(8-(2-hydroxybenzoyl)amino)caprylic acid. The invention further relates to processes for the preparation of such compositions, and their use in medicine.

12 Claims, 2 Drawing Sheets
Specification includes a Sequence Listing.

(56) References Cited

FOREIGN PATENT DOCUMENTS

| | | |
|---|---|---|
| WO | 2006110551 A2 | 10/2006 |
| WO | 2007076319 A2 | 7/2007 |
| WO | 2008011446 A2 | 1/2008 |
| WO | 2008019143 A2 | 2/2008 |
| WO | 2008070543 A1 | 6/2008 |
| WO | 2008080042 A2 | 7/2008 |
| WO | 2008127669 A1 | 10/2008 |
| WO | 2009158412 A2 | 12/2009 |
| WO | 2010020978 A1 | 2/2010 |
| WO | 2010028257 A1 | 3/2010 |
| WO | 2011/084618 A2 | 7/2011 |
| WO | 2011106378 A2 | 9/2011 |
| WO | 2011109784 A1 | 9/2011 |
| WO | 2012062803 A1 | 5/2012 |
| WO | 2012080471 A1 | 6/2012 |
| WO | 12130136 A1 | 10/2012 |
| WO | 2012177929 A2 | 12/2012 |
| WO | 2013022960 A1 | 2/2013 |
| WO | 2013139694 A1 | 9/2013 |
| WO | 2013139695 A1 | 9/2013 |
| WO | 2013189988 A1 | 12/2013 |
| WO | 2014010586 A1 | 1/2014 |
| WO | 2014096150 A1 | 6/2014 |
| WO | 2014177683 A1 | 11/2014 |
| WO | 2015086729 A1 | 6/2015 |
| WO | 2015086732 A1 | 6/2015 |
| WO | 2016055550 A1 | 4/2016 |
| WO | 2016120380 A1 | 8/2016 |
| WO | 2016203495 A1 | 12/2016 |
| WO | 2017060500 A1 | 4/2017 |
| WO | 2017149070 A1 | 9/2017 |
| WO | 2018065634 A1 | 4/2018 |
| WO | 2018076074 A1 | 5/2018 |
| WO | 2019149880 A1 | 8/2019 |

OTHER PUBLICATIONS

Moon et al., "The development of non-peptide glucagon-like peptide-1 receptor agonist for the treatment of type 2 diabetes", Arch Pharm Res, Jul. 2011, vol. 34, No. 7, pp. 1041-1043.

Galstyan et al., "Evolution of glucagon-like peptide-1 receptor agonists in type 2 diabetes therapy", Diabetes, 2017, vol. 20, No. 4, pp. 286-298.

Verbeeck et al., "Generic substitution: The use of medicinal products containing different salts and implications for safety and efficacy", European Journal of Pharmaceutical Sciences, May 2006, vol. 28, No. 1-2, pp. 1-6.

Pertsev et al., "Pharmaceutical and Medical and Biological Aspects of Drugs", Ministry of Health of Ukraine, 1999, vol. 1, p. 253-254.

Lieberman et al., "Chapter 32—Chemical and Physicochemical Approaches to Solve Formulation Problems", The Practice of Medicinal Chemistry, 2015, pp. 767-791.

A

B

SOLID COMPOSITIONS COMPRISING A GLP-1 AGONIST AND A SALT OF N-(8-(2-HYDROXYBENZOYL)AMINO) CAPRYLIC ACID

TECHNICAL FIELD OF THE INVENTION

The present invention relates to solid compositions comprising a GLP-1 agonist and a salt of N-(8-(2-hydroxybenzoyl)amino)caprylic acid, their method of preparation and their use in medicine.

CROSS-REFERENCE TO RELATED APPLICATIONS

This application is a 35 U.S.C. § 371 National Stage application of International Application PCT/EP2019/061502 (WO2019/215063), filed May 6, 2019, which claims priority to European Patent Application 18171046.8, filed May 7, 2018; the contents of which are incorporated herein by reference.

INCORPORATION-BY-REFERENCE OF THE SEQUENCE LISTING

The Sequence Listing, entitled "SEQUENCE LISTING", is 4 KB and was created Apr. 25, 2019 and is incorporated herein by reference.

BACKGROUND

Human GLP-1 and analogues thereof have a low oral bioavailability. Exposure and bioavailability of human GLP-1 and analogues thereof is very low following oral administration. Human GLP-1 and analogues thereof can only reach therapeutically relevant plasma concentration after oral administration if formulated with certain absorption enhancers in a specific amount.

Steinert et al. (Am J Clin Nutr, Oct 2010; 92: 810-817) discloses oral administration of a tablet comprising GLP-1 (7-36)amide and 150 mg sodium N-(8-(2-hydroxybenzoyl) amino)caprylate (SNAC).

WO 2010/020978 discloses an oral pharmaceutical composition comprising a protein and N-(8-[2-hydroxybenzoyl) amino)caprylate (SNAC). Patent applications disclosing oral dosage forms of GLP-1 analogues containing a salt of N-(8-(2-hydroxybenzoyl)amino)caprylate include WO2012/080471, WO2013/189988, WO2013/139694, WO2013/139695 and WO2014/177683.

Despite these findings there is still room for a further optimized pharmaceutical composition for oral administration of a GLP-1 agonist such as a GLP-1 analogue comprising a substituent.

SUMMARY

The present invention in an aspect relates to a composition comprising a GLP-1 agonist, an absorption enhancer or delivery agent and a hydrotrope. The composition according to the invention comprises balanced amounts of the delivery agent and the hydrotrope. The provided compositions display an accelerated absorption, enabling fast and efficient uptake of the active pharmaceutical ingredient.

Oral administration of therapeutic peptides is challenging, due to the rapid degradation of such peptides in the gastrointestinal system.

Described herein are pharmaceutical compositions providing accelerate absorption of the GLP-1 agonist within 15-30 minutes after administration and thereby improved exposure of the GLP-1 agonist by oral administration. The inventors have surprisingly found that an increased exposure of GLP-1 agonists is observed when compositions are prepared with a hydrotrope.

An aspect of the invention relates to a composition comprising
i) a GLP-1 agonist,
ii) a salt of N-(8-(2-hydroxybenzoyl)amino)caprylic acid (NAC) and
iii) a hydrotrope,
wherein the hydrotrope is capable of increasing the solubility of SNAC at least 2-fold, such as 5-fold or such as at least 10-fold.

In one embodiment the composition comprises:
i) 0.1-50 mg GLP-1 agonist, such as Semaglutide, GLP-1 agonist B or GLP-1 agonist C.
ii) 50-600 mg salt of N-(8-(2-hydroxybenzoyl)amino) caprylic acid (NAC), such as the sodium salt of NAC (SNAG) and
iii) 20-200 mg nicotinamide or resorcinol and
iv) 0-10 mg lubricant.

A further aspect relates to a method for producing a solid pharmaceutical composition comprising the steps of;
i) obtaining a blend comprising a salt of NAC and a hydrotrope,
ii) co-processing the blend of i) and
iii) preparing said solid pharmaceutical composition using the product of ii).

A further aspect relates to the medical use of compositions described herein. An embodiment relates to pharmaceutical use of compositions described herein, such as compositions for oral administration. In a further embodiment the composition is a pharmaceutical composition for use in a method of treating diabetes and/or obesity.

In a further aspect the invention relates to a method of treating diabetes or obesity comprising administering the composition as defined herein to a patient in need thereof.

DESCRIPTION

Figure 1:
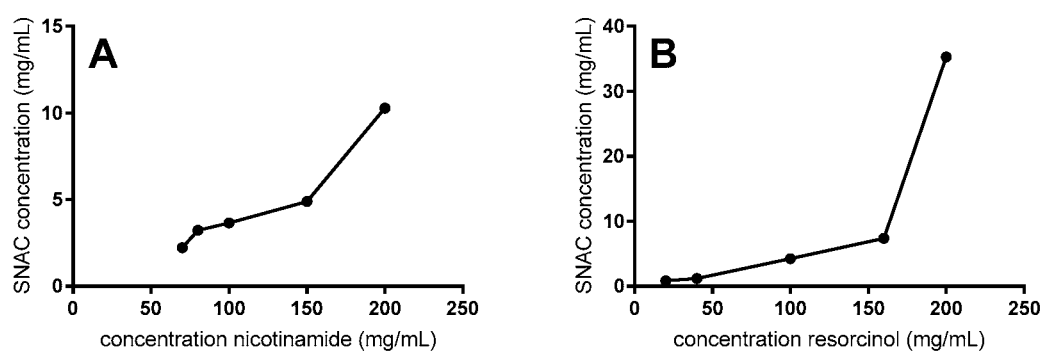
FIG. 1 shows dose dependent effect of nicotinamide (A) and resorcinol (B) on SNAC solubility at pH 6.
Figure 2:
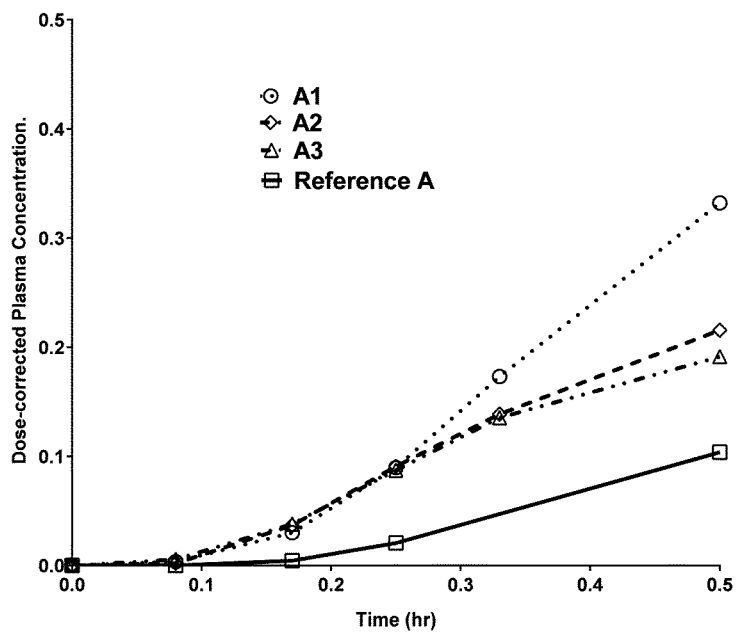
FIG. 2 shows the dose corrected exposure during the first 30 minutes observed in dogs after dosing of formulations with two different GLP-1 agonists, GLP-1 agonist A and B, respectively. Compositions according to the invention all demonstrate an increased dose-corrected exposure relative to the reference compositions.
Figure 2:
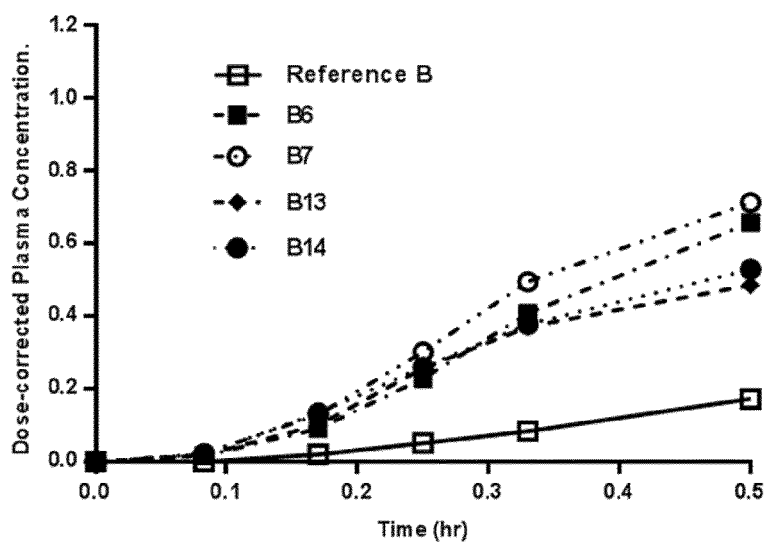

Aspects of the invention described herein relate to a composition comprising a GLP-1 agonist and an absorption enhancer or delivery agent and a hydrotrope. The composition may be in the form suitable for oral administration, such as in a solid form exemplified by a tablet, sachet or capsule. In an embodiment the composition is an oral composition, or a pharmaceutical composition, such as an oral pharmaceutical composition. The provided compositions display an accelerated absorption, enabling fast and efficient uptake of the active pharmaceutical ingredient.

GLP-1

The term "GLP-1 agonist" as used herein refers to a compound, which fully or partially activates the human GLP-1 receptor. The term is thus equal to the term "GLP-1 receptor agonist" used in other documents. The term GLP-1 agonist as well as the specific GLP-1 agonists described herein also encompass salt forms thereof.

It follows that the GLP-1 agonist should display "GLP-1 activity" which refers to the ability of the compound, i.e. a GLP-1 analogue or a compound comprising a GLP-1 analogue, to bind to the GLP-1 receptor and initiate a signal transduction pathway resulting in insulinotropic action or other physiological effects as is known in the art. In some embodiments the "GLP-1 agonist" binds to a GLP-1 receptor, e.g., with an affinity constant ($K_D$) or activate the receptor with a potency ($EC_{50}$) of below 1 µM, e.g. below 100 nM as measured by methods known in the art (see e.g. WO 98/08871) and exhibits insulinotropic activity, where insulinotropic activity may be measured in vivo or in vitro assays known to those of ordinary skill in the art. For example, the GLP-1 agonist may be administered to an animal with increased blood glucose (e.g. obtained using an Intravenous Glucose Tolerance Test (IVGTT). A person skilled in the art will be able to determine a suitable glucose dosage and a suitable blood sampling regime, e.g. depending on the species of the animal, for the IVGTT) and measure the plasma insulin concentration over time. Suitable assays have been described in such as WO2015/155151.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed. Due to the albumin binding effects of GLP-1 agonists comprising a substituent as described herein, it is important to pay attention to if the assay includes human serum albumin or not.

The in vitro potency of the GLP-1 agonist may be determined as described in 2015/155151, example 29 without Human Serum Albumin (HSA), and the $EC_{50}$ determined. The lower the $EC_{50}$ value, the better the potency. In one embodiment the potency (EC50) as determined (without HSA) is 5-1000 pM, such as 10-750 pM, 10-500 pM or 10-200 pM. In one embodiment the EC50 (without HSA) is at most 500 pM, such as at most 300 pM, such as at most 200 pM.

In one embodiment the EC50 (without HSA) is comparable to human GLP-1(7-37).

In one embodiment the EC50 (without HSA) is at most 50 pM. In a further such embodiment the EC50 is at most 40 pM, such as at most 30 pM such as at most 20 pM, such as at most 10 pM. In one embodiment the EC50 is around 10 pM.

Also, or alternatively, the binding of the GLP-1 agonist to albumin may be measured using the in vitro potency assay of Example 29 including HSA. An increase of the in vitro potency, $EC_{50}$ value, in the presence of serum albumin reflects the affinity to serum albumin.

In one embodiment the potency (EC50) as determined (with 1% HSA) is 5-1000 pM, such as 100-750 pM, 200-500 pM or 100-400 pM. In one embodiment the EC50 (with 1% HSA) is at most 750 pM, such as at most 500 pM, such as at most 400 pM, such as at most 300 or such as at most 250 pM.

If desired, the fold variation in relation to a known GLP-1 receptor agonist may be calculated as EC50(test analogue)/EC50(known analogue), and if this ration is such as 0.5-1.5, or 0.8-1.2 the potencies are considered to be equivalent.

In one embodiment the potency, EC50 (without HSA), is equivalent to the potency of liraglutide.

In one embodiment the potency, EC50 (without HSA), is equivalent to the potency of semaglutide.

In one embodiment the potency, EC50 (without HSA), is equivalent to the potency of GLP-1 agonist B. In one embodiment the potency, EC50 (without HSA), is equivalent to the potency of
GLP-1 agonist C.

In one embodiment the potency, EC50 (with 1% HSA), is equivalent to the potency of liraglutide.

In one embodiment the potency, EC50 (with 1% HSA), is equivalent to the potency of semaglutide.

In one embodiment the potency, EC50 (with 1% HSA), is equivalent to the potency of GLP-1 agonist B.

In one embodiment the potency, EC50 (with 1% HSA), is equivalent to the potency of GLP-1 agonist C.

In one embodiment a GLP-1 agonist is a bifunctional molecule such as co-agonist, or tri-agonist.

In one embodiment the GLP-1 agonist is also a Gastric inhibitory polypeptide receptor agonist (GIP agonist). In one embodiment the GLP-1 agonist is Tirzepatide.

In some embodiments the GLP-1 agonist is a GLP-1 analogue, optionally comprising one substituent. The term "analogue" as used herein referring to a GLP-1 peptide (hereafter "peptide") means a peptide wherein at least one amino acid residue of the peptide has been substituted with another amino acid residue and/or wherein at least one amino acid residue has been deleted from the peptide and/or wherein at least one amino acid residue has been added to the peptide and/or wherein at least one amino acid residue of the peptide has been modified. Such addition or deletion of amino acid residues may take place at the N-terminal of the peptide and/or at the C-terminal of the peptide. In some embodiments a simple nomenclature is used to describe the GLP-1 agonist, e.g., [Aib8] GLP-1(7-37) designates an analogue of GLP-1(7-37) wherein the naturally occurring Ala in position 8 has been substituted with Aib. In some embodiments the GLP-1 agonist comprises a maximum of twelve, such as a maximum of 10, 8 or 6, amino acids which have been altered, e.g., by substitution, deletion, insertion and/or modification, compared to e.g. GLP-1(7-37). In some embodiments the analogue comprises up to 10 substitutions, deletions, additions and/or insertions, such as up to 9 substitutions, deletions, additions and/or insertions, up to 8 substitutions, deletions, additions and/or insertions, up to 7 substitutions, deletions, additions and/or insertions, up to 6 substitutions, deletions, additions and/or insertions, up to 5 substitutions, deletions, additions and/or insertions, up to 4 substitutions, deletions, additions and/or insertions or up to 3 substitutions, deletions, additions and/or insertions, compared to e.g. GLP-1(7-37). Unless otherwise stated the GLP-1 comprises only L-amino acids.

In some embodiments the term "GLP-1 analogue" or "analogue of GLP-1" as used herein refers to a peptide, or a compound, which is a variant of the human Glucagon-Like Peptide-1 (GLP-1(7-37)). GLP-1(7-37) has the sequence HAEGTFTSDV SSYLEGQAAKEFIAWLVKGRG (SEQ ID No: 1). In some embodiments the term "variant" refers to a compound which comprises one or more amino acid substitutions, deletions, additions and/or insertions.

In one embodiment the GLP-1 agonist exhibits at least 60%, 65%, 70%, 80% or 90% sequence identity to GLP-1 (7-37) over the entire length of GLP-1(7-37). As an example of a method for determination of sequence identity between two analogues the two peptides [Aib8]GLP-1(7-37) and GLP-1(7-37) are aligned. The sequence identity of [Aib8]

GLP-1(7-37) relative to GLP-1(7-37) is given by the number of aligned identical residues minus the number of different residues divided by the total number of residues in GLP-1 (7-37). Accordingly, in said example the sequence identity is (31-1)/31.

In one embodiment the C-terminal of the GLP-1 agonist is an amide.

In some embodiments the GLP-1 agonist is GLP-1(7-37) or GLP-1(7-36)amide. In some embodiments the GLP-1 agonist is exendin-4, the sequence of which is HGEGT-FITSDLSKQMEEEAVRLFIEWLKNGGPSSGAPPPS (SEQ ID No: 2). In one embodiment the GLP-1 agonist is an exendin-4 analogue or an engineered peptide thereof, as disclosed in WO2013009545 and references therein.

In order to prolong the effect of the GLP-1 agonist it is preferred that the GLP-1 agonist have an extended half-life. The half-life can be determined by method known in the art an in an appropriate model, such as in Male Sprague Dawley rats or minipigs as described in WO2012/140117. Half-life in rats may be determined as in Example 39 and the half-life in minipigs may be determined as in Example 37 therein.

In one embodiment the GLP-1 agonist according to the invention has a half-life above 2 hours in rat. In one embodiment the GLP-1 agonist according to the invention has a half-life above 4 hours, such as above 6 hours, such as above 8 hours, such as above 10 hours, such as above 12 hours or such as above 15 hours in rat.

In one embodiment the GLP-1 agonist according to the invention has a half-life above 24 hours in minipig. In one embodiment the GLP-1 agonist according to the invention has a half-life above 30 hours, such as above 36 hours, such as above 42 hours, such as above 48 hours, such as above 54 hours or such as above 60 hours in minipig.

In one embodiment the GLP-1 agonist has a molecular weight of at most 50 000 Da, such as at most 40 000 Da, such as at most 30 000 Da.

In one embodiment the GLP-1 agonist has a molecular weight of at most 20 000, such as at most 10 000 Da, such as at most 7 500 Da, such as at most 5 000 Da.

In one embodiment the GLP-1 agonist has a molar mass of at most 50 000 g/mol, such as at most 40 000 g/mol, such as at most 30 000 g/mol.

In one embodiment the GLP-1 agonist has a molar mass of at most 10 000 g/mol, such as at most 8 000 g/mol, such as at most 6 000 g/mol.

In some embodiments the GLP-1 agonist comprises one substituent which is covalently attached to the peptide. In some embodiments the substituent comprises a fatty acid or a fatty diacid. In some embodiments the substituent comprises a C16, C18 or C20 fatty acid. In some embodiments the substituent comprises a C16, C18 or C20 fatty diacid.

In some embodiments the substituent comprises formula (X)

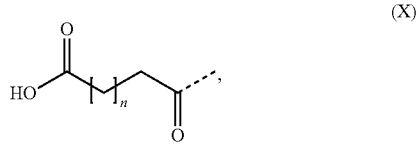

wherein n is at least 13, such as n is 13, 14, 15, 16, 17, 18 or 19. In some embodiments the substituent comprises formula (X), wherein n is in the range of 13 to 19, such as in the range of 13 to 17. In some embodiments the substituent comprises formula (X), wherein n is 13, 15 or 17. In some embodiments the substituent comprises formula (X), wherein n is 13. In some embodiments the substituent comprises formula (X), wherein n is 15. In some embodiments the substituent comprises formula (X), wherein n is 17.

In some embodiments the substituent comprises formula (XIa)

HOOC—($C_6H_4$)—O—($CH_2$)$_m$—CO—*   (XIa), wherein m is an integer in the range of 6-14

In some embodiments the substituent comprises formula (XIb)

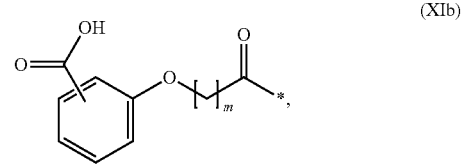

wherein the carboxy group is in position 2, 3 or 4 of the ($C_6H_4$) group and wherein m is an integer in the range of 8-11.

In some embodiments the substituent comprises formula (XIa) or formula (XIb), wherein m is in the range of 6 to 14, such as in the range of 8 to 11. In some embodiments the substituent comprises formula (XIa) or formula (XIb), wherein m is 8, 10 or 12. In some embodiments the substituent comprises formula (XIa) or formula (XIb), wherein m is 9. In some embodiments the substituent comprises formula (XIa) or formula (XIb), wherein m is 11.

In some embodiments the substituent comprises one or more 8-amino-3,6-dioxaoctanoic acid (OEG), such as two OEG.

In some embodiments the substituent is [2-(2-{2-[2-(2-{2-[(S)-4-carboxy-4-(17-carboxyheptadecanoylamino) butyrylamino]ethoxy}ethoxy)acetylamino] ethoxy}ethoxy) acetyl].

In some embodiments the substituent is [2-(2-{2-[2-(2-{2-[(S)-4-carboxy-4-({trans-4-[(19-carboxynonadecanoy-lamino)methyl]cyclohexanecarbonyl} amino)butyrylamino] ethoxy}ethoxy)acetylamino]ethoxy}ethoxy)acetyl].

In some embodiments the GLP-1 agonist is semaglutide, also known as N-epsilon26-[2-(2-{2-[2-2-{2-[(S)-4-car-boxy-4-(17-carboxyheptadecanoylamino) butyrylamino] ethoxy}ethoxy)acetylamino]ethoxy}ethoxy)acetyl][Aib8, Arg34]GLP-1(7-37), (SEQ ID NO. 4) which may be prepared as described in WO2006/097537, Example 4 with the following structure:

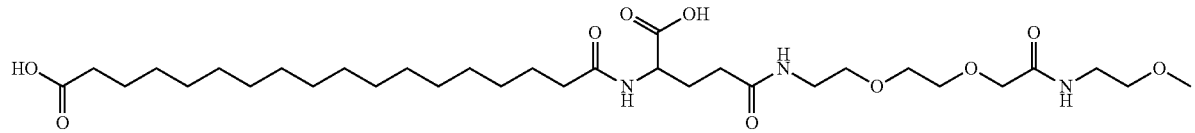
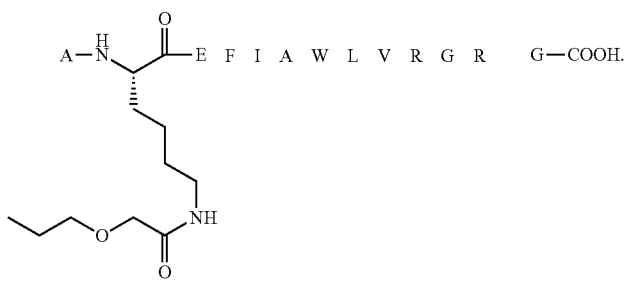

In one embodiment the GLP-1 agonist is GLP-1 agonist B, which is diacylated [Aib8,Arg34,Lys37]GLP-1(7-37) (SEQ ID NO. 5) as shown in Example 2 of WO2011/080103 and named $N^{\varepsilon 26}$\{2-[2-(2-\{2-[2-(2-\{(S)-4-Carboxy-4-[10-(4-carboxyphenoxy)decanoylamino]butyrylamino\}-ethoxy)ethoxy]acetylamino\}ethoxy)ethoxy]acetyl\}, $N^{\varepsilon 37}$-\{2-[2-(2-\{2-[2-(2-\{(S)-4-carboxy-4-[10-(4-carboxyphenoxy)decanoylamino]butyrylamino\}ethoxy)ethoxy]acetylamino\}ethoxy)ethoxy]-acetyl\}-[Aib$^8$,Arg$^{34}$,Lys$^{37}$] GLP-1(7-37)—peptide with the following structure.

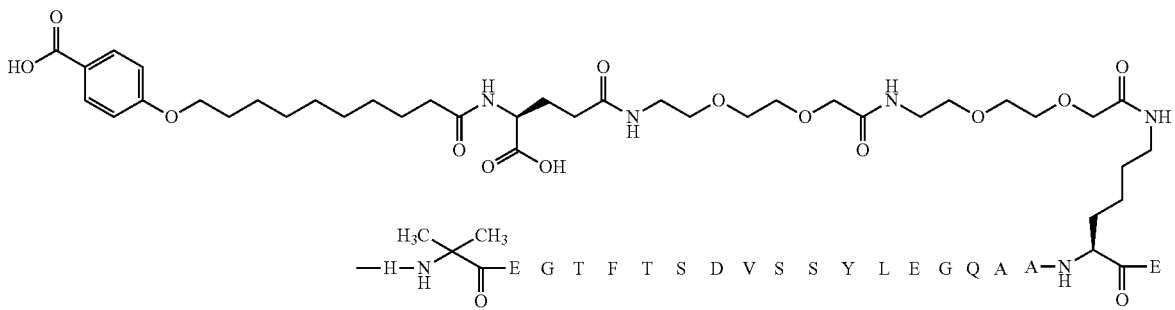
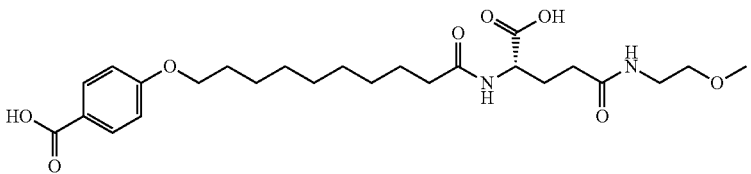
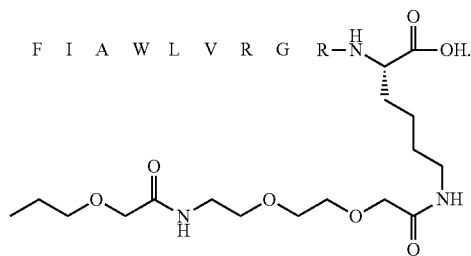

In one embodiment the GLP-1 agonist is GLP-1 agonist C which is Diacylated [Aib8,Glu22,Arg26,Lys27,Glu30, Arg34,Lys36]-GLP-1-(7-37)-peptidyl-Glu-Gly (SEQ ID NO. 6) as shown in Example 31 of WO2012/140117 and named N$^{\varepsilon 27}$-[2-[2-[2-[[2-[2-[2-[[(4S)-4-carboxy-4-[10-(4-carboxyphenoxy)decanoylamino]butanoyl]amino] ethoxy] ethoxy]acetyl]amino]ethoxy]ethoxy]-acetyl], N$^{\varepsilon 36}$-[2-[2-[2-[[2-[2-[2-[[(4S)-4-carboxy-4-[10-(4-carboxyphenoxy)decanoylamino]-butanoyl]amino]ethoxy]ethoxy]acetyl] amino]ethoxy]ethoxy]acetyl]-[Aib8,Glu22,Arg26,Lys27, Glu30,Arg34,Lys36]-GLP-1-(7-37)-peptidyl-Glu-Gly with the following structure:

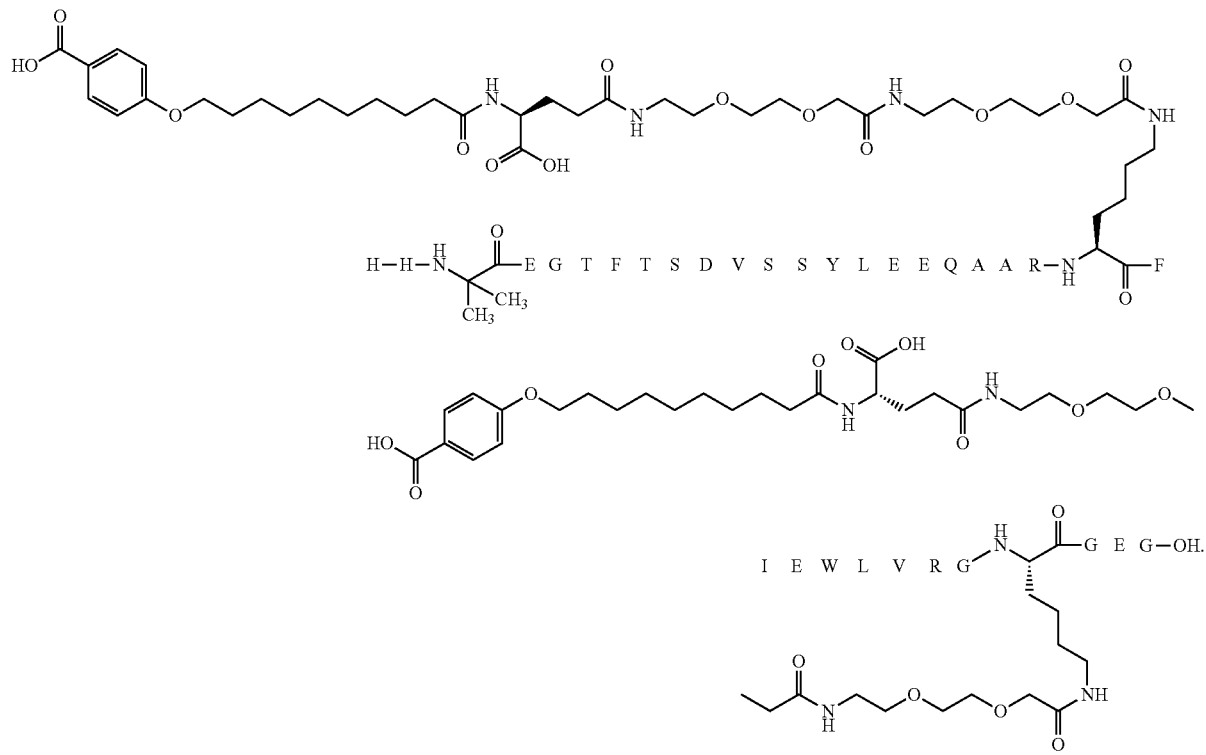

In general, the term GLP-1 agonist is meant to encompass the GLP-1 agonist and any pharmaceutically acceptable salt, amide, or ester thereof. In some embodiments the composition comprises the GLP-1 agonist or a pharmaceutically acceptable salt, amide, or ester thereof. In some embodiments the composition comprises the GLP-1 agonist and one or more pharmaceutically acceptable counter ions.

In some embodiments the GLP-1 agonist is selected from one or more of the GLP-1 agonists mentioned in WO93/19175, WO96/29342, WO98/08871, WO99/43707, WO99/43706, WO99/43341, WO99/43708, WO2005/027978, WO2005/058954, WO2005/058958, WO2006/005667, WO2006/037810, WO2006/037811, WO2006/097537, WO2006/097538, WO2008/023050, WO2009/030738, WO2009/030771 and WO2009/030774.

In some embodiments the GLP-1 agonist is selected from the group consisting of N-epsilon37{2-[2-(2-{2-[2-((R)-3-carboxy-3-{[1-(19-carboxynonadecanoyl) piperidine-4-carbonyl]amino}propionylamino)ethoxy]ethoxy}acetylamino] ethoxy]ethoxy}acetyl [desaminoHis7,Glu22,Arg26,Arg34, Lys37]GLP-1(7-37)amide; N-epsilon26{2-[2-(2-{2-[2-((R)-3-carboxy-3-{[1-(19- carboxynonadecanoyl) piperidine-4-carbonyl]amino} propionylamino)ethoxy] ethoxy}acetyl [desaminoHis7, Arg34] GLP-1-(7-37); N-epsilon37{2-[2-(2-2-[2-((S)-3-carboxy-3-{[1-(19-carboxy-nonadecanoyl) piperidine-4-carbonyl]amino}propionylamino)ethoxy] ethoxy} acetylamino) ethoxy] ethoxy}acetyl[Aib8,Glu22,Arg26,Arg34,Lys37] GLP-1-(7-37)amide; N-epsilon37-[2-(2-[2-(2-[2-(2-((R)-3-[1-(17-carboxyheptadecanoyl)piperidin-4-ylcarbonylamino]3-carboxypropionylamino)ethoxy)ethoxy] acetylamino)ethoxy] ethoxy)acetyl][,DesaminoHis7, Glu22 Arg26, Arg 34, Phe(m-CF3)28]GLP-1-(7-37)amide; N-epsilon26-[(S)-4-carboxy-4-({trans-4-[(19-carboxynonade- canoylamino)methyl] cyclohexanecarbonyl}amino)butyryl] [Aib8,Arg34]GLP-1-(7-37); N-epsilon26-{4-[(S)-4-carboxy-4-({trans-4-[(19-carboxynonadecanoylamino) methyl]cyclohexanecarbonyl} amino)butyrylamino]bu- tyryl}[Aib8,Arg34]GLP-1-(7-37); N-epsilon2642-(2-{2-[(S)-4-carboxy-4-({trans-4-[(19-carboxy-nonadecanoy- lamino) methyl]cyclohexanecarbonyl} amino) butyrylamino]ethoxy}ethoxy)acetyl][Aib8,Arg34]GLP-1 -(7-37); N-epsilon26-[2-(2-{2-[2-(2-{2-[(S)-4-carboxy-4- trans-4-[(19-carboxy-nonadecanoylamino)methyl] cyclohexanecarbonyl}amino)butyrylamino]ethoxy}ethoxy) acetylamino]ethoxy}ethoxy) acetyl][Aib8,Arg34]GLP-1- (7-37)amide; N-epsilon37-[2-(2-{2[2-(2-{2-[(S)-4-carboxy- 4-({trans-4-[(19-carboxy-nonadecanoylamino)methyl] cyclohexanecarbonyl}amino) butyrylamino]ethoxy}ethoxy) acetylamino]ethoxy}ethoxy)acetyl][Aib8,Glu22,Arg26, Arg34,Lys37]GLP-1-(7-37)amide; N-epsilon37-[2-(2-{2- [2-(2-{2-[(S)-4-carboxy-4-({trans-4-[(19-carboxy-nonade- canoylamino)methyl]cyclohexanecarbonyl}amino) butyry- lamino] ethoxy}ethoxy)acetylamino]ethoxy}ethoxy)acetyl] [DesaminoHis7,Glu22, Arg26,Arg34,Lys37]GLP-1(7-37) amide; N-epsilon37-[2-(2-{2-[2-(2-{2-[(S)-4-carboxy-4-

({4-[(trans-19-carboxy-nonadecanoylamino)methyl]cyclohexanecarbonyl}amino) butyrylamino]ethoxy}ethoxy)acetyl][DesaminoHis7,Arg26,Arg34,L ys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,A rg34,Lys37]GLP-1-(7-37); N-epsilon26[2-(2-{2-[2-(2-{2-[(S)-4-carboxy-4-({4-[(19-carboxy-nonadecanoylamino)methyl]cyclohexanecarbonyl}amino)butyrylamino] ethoxy}ethoxy)acetylamino]ethoxy}ethoxy)acetyl[Aib8, Lys 26]GLP-1 (7-37)amide; N-epsilon26 [2-(2-[2-(2-[2-(2-((S)-2-[trans-4-((9- carboxynonadecanoylamino] methyl) cyclohexylcarbonylamino]-4-carboxybutanoylamino)ethoxy)ethoxy]acetylamino) ethoxy]ethoxy)acetyl][Aib8, Lys26] GLP-1 (7-37) amide; N-epsilon37-[2-(2-{2-[2-(2-{2-[(S)-4-carboxy-4-({trans-4-[(19-carboxy-nonadecanoylamino)methyl]cyclohexane-carbonyl} amino)butyrylamino]ethoxy}ethoxy)acetylamino]ethoxy}ethoxy)acetyl] [DesaminoHis7,Arg26,Arg34,Lys37]GLP-1-(7-37); N-epsilon37-[2-(2-{2-[2-(2-{2-[(S)-4-carboxy-4-({trans-4-[(19-carboxy-nonadecanoylamino)methyl]cyclohexanecarbonyl} amino)butyrylamino]ethoxy}ethoxy)acetylamino]ethoxy}ethoxy)acetyl][DesaminoHis7,Glu22, Arg26,Glu30, Arg34,Lys37]GLP-1-(7-37); N-epsilon26-[2-(2-{2-[(S)-4-carboxy-4-((S)-4-carboxy-4-{4-[4-(16-(1H-tetrazol-5-yl)-hexadecanoylsulfamoyl)butyrylamino]-butyrylamino}butyrylamino) butyrylamino] ethoxy}ethoxy) acetyl][Aib8,Arg34]GLP-1-(7-37); N-epsilon26-[2-(2-{2-[(S)-4-carboxy-4-((S)-4-carboxy-4-{12[4-(16-(1H-tetrazol-5-yl)hexadecanoyl-sulfamoyl)butyrylamino]dodecanoylamino}butyrylamino) butyrylamino] ethoxy}ethoxy)acetyl][Aib8,Arg34]GLP-1-(7-37); N-epsilon26-[2-(2-{2-[(S)-4-carboxy-4-((S)-4-carboxy-4-{6-[4-(16-(1H-tetrazol-5-yl)hexadecanoyl-sulfamoyl)butyrylamino]hexanoylamino} butyrylamino)butyrylamino] ethoxy}ethoxy) acetyl][Aib8,Arg34]GLP-1-(7-37); N-epsilon26-[2-(2-{2-[(S)-4-carboxy-4-((S)-4-carboxy-4-{4-[4-(16-(1H-tetrazol-5-yl)hexadecanoylsulfamoyl)butyrylamino] butyrylamino}butyrylamino)butyrylamino] ethoxy}ethoxy)acetyl][Aib8,Arg34]GLP1-(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]-dodecanoylamino}butyrylamino) butyrylamino] ethoxy}ethoxy)acetyl][Aib8,Arg34]GLP-1-(7-34); N-epsilon26-[2-(2-{2-[(S)-4-carboxy-4-((S)-4-carboxy-4-{6-[4-(16-(1H-tetrazol-5-yl) hexadecanoylsulfamoyl) butyrylamino]hexanoylamino}butyrylamino) butyrylamino]ethoxy}ethoxy)acetyl] [Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino} butyrylamino)butyrylamino] ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol yl)hexadecanoylsulfamoyl)butyrylamino]hexanoylamino} butyrylamino)butyrylamino] ethoxy}ethoxy)acetyl][Aib8,Arg34]GLP-1-(7-35); N-epsilon26[2-(2-{2-[(S)-4-carboxy-4-((S)-4-carboxy-4-{6-[4-(16-(1H-tetrazol-5-yl)hexadecanoylsulfamoyl)butyrylamino] hexanoylamino}butyrylamino)butyrylamino] ethoxy}ethoxy)acetyl][Aib8,Arg34]GLP-1-(7-36)amide; N-epsilon26-[2-(2-{2-[(S)-4-carboxy-4-((S)-4-carboxy-4-{6-[4-(16-(1H-tetrazol-5-yl)hexadecanoylsulfamoyl) butyrylamino]hexanoylamino}butyrylamino) butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyryl-amino)butyrylamino]ethoxy} ethoxy)acetyl][Aib8,Lys33,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-36)amide; N-epsilon26-[2-(2-{2-[2-(2-{2-[2-(2-{2-[2-(2-{2-[2-(2-{2-[2-(2-{2-[(S)-4-carboxy-4-((S)-4-carboxy-4-{12-[4-(16-(1H-tetrazol-5-yl)hexadecanoylsulfamoyl) butyrylamino]dodecanoylamino}butyrylamino) butyrylamino] ethoxy} acetylamino]ethoxy}ethoxy)acetylamino] ethoxy}ethoxy)acetylamino]ethoxy}ethoxy)acetylamino]ethoxy}ethoxy)acetyl][Aib8, Lys26,Arg34]GLP-1-(7-36)amide; N-epsilon37-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino}butyrylamino) butyrylamino] ethoxy}ethoxy)acetyl][Aib8,Glu22,Arg26,Arg34,Lys37] GLP-1-(7-37)amide; N-epsilon37-[2-(2-{2-[(S)-4-carboxy-4-((S)-4-carboxy-4-{12-[4-(16-(1H-tetrazol-5-yl) hexadecanoylsulfamoyl)butyrylamino]dodecanoylamino}butyrylamino) butyrylamino] ethoxy}ethoxy)acetyl][DesaminoHis7,Glu22,Arg26,Arg34, Lys37]GLP-1-(7-37)amide; N-epsilon37{2-[2-(2-{2-[2-((R)-3-carboxy-3-{[1-(19-carboxy-nonadecanoyl) piperidine-4-carbonyl]amino}propionylamino)ethoxy]ethoxy}acetylamino)ethoxy] ethoxy}acetyl [desaminoHis7,Glu22, Arg26,Arg34,Lys37]GLP1(7-37)amide; N-epsilon37{2-[2-(2-{2-[2-((S)-3-carboxy-3-{[1-(19-carboxynonadecanoyl) piperidine-4-carbonyl]amino} propionylamino) ethoxy]ethoxy}acetylamino)ethoxy] ethoxy} acetyl [Aib8,Glu22, Arg26,Arg34, Lys37]GLP-1-(7-37)amide; N-epsilon37-[2-(2-[2-[2-(2-((R)-3-[1-(17-carboxyhepta-decanoyl)piperidin-4-ylcarbonylamino]3-carboxy-propionylamino) ethoxy) ethoxy] acetylamino) ethoxy] ethoxy)acetyl] [DesaminoHis7, Glu22,Arg26, Arg34,Phe(m-CF3)28] GLP-1-(7-37)amide; N-epsilon37-[2-(2-{2-[2-(2-{2-[(S)-4-carboxy-4-({trans-4-[(19-carboxy-nonadecanoylamino) methyl] cyclohexanecarbonyl} amino)butyrylamino] ethoxy} ethoxy)acetylamino] ethoxy}ethoxy)acetyl] [Aib8, Glu22,Arg26,Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexane-carbonyl} amino)butyrylamino]ethoxy}ethoxy) acetylamino] ethoxy}ethoxy)acetyl] [DesaminoHis7,Glu22,Arg26, Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl] cyclohexanecarbonyl}amino) butyrylamino]ethoxy}ethoxy) acetylamino]ethoxy} ethoxy) acetyl] [DesaminoHis7,Glu22,Arg26,Arg34, Lys37]GLP-1-(7-37); N-epsilon37-[2-(2-{2-[2-(2-{2-[(S)-4-carboxy-4-({trans-4-[(19-carboxy-nonadecanoylamino) methyl] cyclohexane-carbonyl}amino)butyrylamino] ethoxy}ethoxy) acetylamino] ethoxy}ethoxy)acetyl] [DesaminoHis7,Glu22,Arg26,Glu30,Arg34, Lys37]GLP-1-(7-37); N-epsilon37-[2-(2-{2-[(S)-4-carboxy-4-((S)-4-carboxy-4-{12-[4-(16-(1H-tetrazol-5-yl)hexadecanoyl-sulfamoyl) butyrylamino]dodecanoylamino} butyrylamino) butyrylamino] ethoxy}ethoxy)acetyl] [Aib8,Glu22,Arg26, Arg34,Lys37]GLP-1-(7-37)amide; N-epsilon37-[2-(2-{2-[(S)-4-carboxy-4-((S)-4-carboxy-4-{12-[4-(16-(1H-tetrazol-5-yl)hexadecanoylsulfamoyl) butyrylamino] dodecanoylamino}butyrylamino) butyrylamino] ethoxy}ethoxy)acetyl] [DesaminoHis7,Glu22,Arg26, Arg34,Lys37]GLP-1-(7-37)amide; N-epsilon37-(3-((2-(2-

(2-(2-(2-Hexadecyloxyethoxy)ethoxy)ethoxy) ethoxy)) propionyl)[DesaminoHis7,Glu22,Arg26,Arg34, Lys37]GLP-1(7-37)-amide; N-epsilon37-{2-(2-(2-(2-[2-(2-(4-(hexadecanoylamino)-4-carboxybutyryl-amino)ethoxy) ethoxy] acetyl)ethoxy)ethoxy)acetyl)}-[desaminoHis7, Glu22,Arg26, Glu30,Arg34,Lys37] GLP-1-(7-37)amide; N-epsilon37-{2-(2-(2-(2-[2-(2-(4-(hexadecanoylamino)-4-carboxy-butyryl-amino) ethoxy)ethoxy]acetyl)ethoxy) ethoxy) acetyl)}-[desaminoHis7,Glu22, Arg26, Arg34, Lys37]GLP-1-(7-37)amide; N-epsilon37-(2-(2-(2-(2-(2-(2-(2-(2-(2-octadecanoyl-amino)ethoxy)ethoxy) acetylamino) ethoxy) ethoxy)acetylamino) ethoxy)ethoxy) acetyl) [desaminoHis7,Glu22,Arg26,Arg34,Lys37] GLP-1 (7-37) amide; N-epsilon37-[4-(16-(1H-Tetrazol-5-yl) hexadecanoylsulfamoyl) butyryl] [DesaminoHis7,Glu22, Arg26, Arg34, Lys37]GLP-1-(7-37)amide; N-epsilon37-[2-(2-{2-[2-(2-{2-[(S)-4-carboxy-4-(19-carboxynonadecanoylamino) butyrylamino] ethoxy}ethoxy) acetylamino]ethoxy} ethoxy)acetyl] [DesaminoHis7,Glu22, Arg26, Arg34,Lys37]GLP-1-(7-37); N-epsilon37-(2-{2-[2-((S)-4-carboxy-4-{(S)-4-carboxy-4-[(S)-4-carboxy-4-(19-carboxy-nonadecanoylamino)butyrylamino]butyrylamino} butyrylamino]ethoxy}ethoxy} acetyl)[DesaminoHis7, Glu22,Arg26,Arg34,Lys37]GLP-1-(7-37); N-epsilon37-{212-(2-{(S) [(S)-4-(12-{4-[16-(2-tert-Butyl-2H-tetrazol-5-yl)-hexadecanoylsulfamoyl] butyrylamino}dodecanoylamino)-4-carboxybutyrylamino]-4-carboxybutyrylamino} ethoxy)ethoxy] acetyl}DesaminoHis7,Glu22,Arg26,Arg34,Lys37] GLP-1 (7-37); N-epsilon37-[2-(2-{2-[2-(2-{2-[(S)-4-carboxy-4-(17-carboxy-heptadecanoylamino)-butyrylamino]ethoxy}-ethoxy)-acetylamino]-ethoxy}-ethoxy)-acetyl] [Aib8, Glu22, Arg26,Arg34,Lys37]GLP-1-(7-37); N-alpha37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Aib8,Glu22,Arg26, Arg34,epsilon-Lys37]GLP-1-(7-37)peptide; N-epsilon37-[2-(2-{2-[2-(2-{2-[(S)-4-carboxy-4-(17-carboxy-heptadecanoylamino)-butyrylamino]-ethoxy}-ethoxy)-acetylamino]ethoxy}-ethoxy)-acetyl] [desaminoHis7, Glu22,Arg26,Arg34,Lys37] GLP-1-(7-37); N-epsilon36[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [desaminoHis7, Glu22, Arg26,Glu30,Arg34,Lys36] GLP-1-(7-37)-Glu-Lys peptide; N-epsilon37-[2-(2-{2-[2-(2-{2-[(S)-4-carboxy-4-({trans-4-[(19-carboxynonadecanoylamino)methyl] cyclohexanecarbonyl}amino)butyryl-amino] ethoxy}ethoxy)acetylamino]ethoxy}ethoxy)acetyl][Aib8, Glu22,Arg26,Arg34,Lys37]GLP -1-(7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl]Aib8,Glu22, Arg26, Arg34,Aib35,Lys37]GLP-1-(7-37); N-epsilon37-[(S)-4-carboxy-4-(2-{2-[2-(2-{2-[2-(17-carboxyheptadecanoylamino) ethoxy] ethoxy} acetylamino) ethoxy] ethoxy} acetylamino) butyryl] [Aib8,Glu22,Arg26, 34,Lys37] GLP-1 (7-37); N-epsilon37-[2-(2-[2-(2-[2-(2-[4-(17-carboxyheptadecanoylamino)-4(S)-carboxybutyrylamino]ethoxy)ethoxy]acetylamino)ethoxy]ethoxy)acetyl] [ImPr7,Glu22, Arg26,34,Lys37], GLP-1-(7-37); N-epsilon26-{2-[2-(2-{2-[2-(2-{(S)-4-carboxy-4-[10-(4-carboxy-phenoxy) decanoylamino]butyrylamino}ethoxy)ethoxy] acetylamino}ethoxy) ethoxy]acetyl}, N-epsilon37-{2-[2-(2-{2-[2-(2-{(S)-4-carboxy-4-[10-(4-carboxy-phenoxy) decanoylamino] butyrylamino}ethoxy)ethoxy] acetylamino}ethoxy) ethoxy]acetyl}-[Aib8,Arg34,Lys37] GLP-1(7-37)-OH; N-epsilon26 (17-carboxyhepta-decanoyl)-[Aib8,Arg34]GLP-1-(7-37)-peptide; N-epsilon26-(19-carboxynonadecanoyl)-[Aib8,Arg34]GLP-1-(7-37); N-epsilon26-(4-{[N-(2-carboxyethyl)-N-(15-carboxypenta-decanoyl)amino]methyl}benzoyl[Arg34]GLP-1-(7-37); N-epsilon26-[2-(2[2-(2-[2-(2-[4-(17-carboxyheptadecanoyl-amino)-4(S)-carboxybutyrylamino]ethoxy)ethoxy] acetyl-amino) ethoxy]ethoxy)acetyl][Aib8,Arg34]GLP-1-(7-37); N-epsilon26-[2-(2-[2-(2-[2-(2-[4-(19-carboxynonadecanoy-lamino)-4(S)-carboxybutyrylamino]ethoxy)ethoxy] acetyl-amino)ethoxy]ethoxy)acetyl][Aib8,Arg34]GLP (7-37); N-epsilon26-[2-(2-[2-(2-[2-(2-[4-(17-carboxyheptade-canoylamino)-4(S)-carboxybutyrylamino]ethoxy)ethoxy] acetylamino)ethoxy]ethoxy)acetyl][3-(4-Imidazolyl)Pro-pionyl7,Arg34]GLP-1-(7-37); N-epsilon26-[2-(2-[2-(2-[2-(2-[4-(17-carboxyheptadecanoylamino)-(carboxymethyl-amino)acetylamino]ethoxy)ethoxy]acetylamino)ethoxy] ethoxy)acetyl][Aib8,Arg34]GLP-1-(7-37); N-epsilon26-[2-(2-[2-(2-[2-(2-[4-(17-carboxyheptadecanoylamino)-3(S)-Sulfopropionylamino]ethoxy)ethoxy]acetylamino)ethoxy] ethoxy)acetyl][Aib8,Arg34]GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy] ethoxy)acetyl][Gly8,Arg34] GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy] ethoxy)acetyl][Aib8,Arg34]GLP-1-(7-37)-amide; N-epsilon26-[2-(2-[2-(2-[2-(2-[4-(17-carboxyheptade-canoylamino)-4(S)-carboxybutyrylamino]ethoxy)ethoxy] acetylamino)ethoxy]ethoxy)acetyl] [Aib8,Arg34,Pro37] GLP-1-(7-37)amide; Aib8,Lys26(N-epsilon26-{2-(2-(2-(2-[2-(2-(4-(pentadecanoylamino)-4-carboxybutyrylamino) ethoxy)ethoxy]acetyl)ethoxy) ethoxy)acetyl)}), Arg34) GLP-1 H(7-37)-OH; N-epsilon26-[2-(2-[2-(2-[2-(2-[4-{[N-(2-carboxyethyl)-N-(17-carboxyheptadecanoyl)amino] methyl}benzoyl)amino]ethoxy) ethoxy]acetylamino) ethoxy]ethoxy)acetyl][Aib8,Arg34]GLP-1(7-37); N-alpha7-formyl, N-epsilon26-[2-(2-[2-(2-[2-(2-[4-(17-car-boxyheptadecanoyl-amino)-4(S)-carboxy-butyrylamino] ethoxy)ethoxy]acetylamino)ethoxy]ethoxy)acetyl] [Arg34] GLP-1-(7-37); N-epsilon2626-[2-(2-[2-(2-[2-(2-[4-(17-carboxyheptadecanoylamino)-4(S)-carboxy-butyrylamino] ethoxy)ethoxy]acetylamino)ethoxy]ethoxy)acetyl][Aib8, Glu22, Arg34) GLP-1-(7-37); N-epsilon26{3-[2-(2-{2-[2-(2-{2-[2-[2-[4-(15-N-((S)-1,3-dicarboxypropyl) carbam-oyl)pentadecanoylamino)-(S)-4-carboxybutyrylamino ethoxy)ethoxy} ethoxy}ethoxy)ethoxy]ethoxy}ethoxy) ethoxy]propionyl}[Aib8,Arg34]GLP-1-(7-37); N-epsi-lon26-[2-(2-[2-(2-[2-(2-[4-{[N-(2-carboxyethyl)-N-(17-car-boxy-heptadecanoyl)amino]methyl}benzoyl)amino](4(S)-carboxybutyryl-amino)ethoxy) ethoxy]acetylamino)ethoxy] ethoxy)acetyl][Aib8,Arg34] GLP-1(7-37); N-epsilon26-{(S)-4-carboxy-4-((S)-4-carboxy-4-((S)-4-carboxy-4-((S)-4-carboxy-4-(19-carboxy-nonadecanoylamino)butyry-lamino)butyrylamino)butyrylamino) butyrylamino}[Aib8, Arg34]GLP-1-(7-37); N-epsilon26-4-(17-carboxyheptadecanoyl-amino)-4(S)-carboxybutyryl-[Aib8, Arg34]GLP-1(7-37); N-epsilon26-{3-[2-(2-{2-[2-(2-{2-[2-[4-(17-carboxyheptadecanoylamino)-4(S)-carboxybutyrylamino]ethoxy)ethoxy]ethoxy}ethoxy) ethoxy]ethoxy}ethoxy)ethoxy]propionyl}[Aib8,Arg34] GLP-1-(7-37); N-epsilon26-{2-(2-(2-(2-[2-(2-(4-(17-carboxyheptadecanoylamino)-4-carboxybutyrylamino) ethoxy)ethoxy)acetyl)}-[Aib8,22,27, 30,35,Arg34,Pro37, Lys26] GLP-1 (7-37)amide; N-epsi-lon26-[2-2-[2-4-(21-carboxyuneicosanoylamino)-4(S)-carboxybutyrylamino]ethoxy]ethoxy)acetyl][Aib8,Arg34]

GLP-1-(7-37); and N-epsilon26-[2-(2-[2-(2-[2-(2-[4-(21-carboxyuneicosanoylamino)-4(S)-carboxybutyrylamino]ethoxy)ethoxy]acetylamino)ethoxy]ethoxy)acetyl][Aib8,Arg34]GLP-1-(7-37).

Delivery Agent

A delivery agent or absorption enhancer is for the present invention an excipient capable of increasing the oral exposure of the GLP-1 agonist.

Salt of N-(8-(2-hydroxybenzoyl)amino)caprylic Acid

The delivery agent used in the present invention is a salt of N-(8-(2-hydroxybenzoyl)amino)caprylic acid (also referred to herein as a salt of NAC), which contains the anion N-(8-(2-hydroxybenzoyl)amino)caprylate. The structural formula of N-(8-(2-hydroxybenzoyl)amino)caprylate is shown in formula (I).

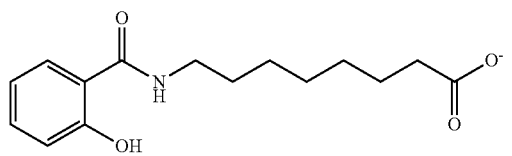

(I)

In some embodiments the salt of N-(8-(2-hydroxybenzoyl)amino)caprylic acid comprises one monovalent cation, two monovalent cations or one divalent cation. In some embodiments the salt of N-(8-(2-hydroxybenzoyl)amino)caprylic acid is selected from the group consisting of the sodium salt, potassium salt and/or calcium salt of of N-(8-(2-hydroxybenzoyl)amino)caprylic acid.

In one embodiment the salt of N-(8-(2-hydroxybenzoyl)amino)caprylic acid is selected from the group consisting of the sodium salt, potassium salt and/or the ammonium salt. In one embodiment the salt of N-(8-(2-hydroxybenzoyl)amino)caprylic acid is the sodium salt or the potassium salt. Salts of N-(8-(2-hydroxybenzoyl)amino)caprylate may be prepared using the method described in e.g. WO96/030036, WO00/046182, WO01/092206 or WO2008/028859.

The salt of N-(8-(2-hydroxybenzoyl)amino)caprylic acid may be crystalline and/or amorphous. In some embodiments the delivery agent comprises the anhydrate, monohydrate, dihydrate, trihydrate, a solvate or one third of a hydrate of the salt of N-(8-(2-hydroxybenzoyl)amino)caprylic acid as well as combinations thereof. In some embodiments the delivery agent is a salt of N-(8-(2-hydroxybenzoyl)amino)caprylic acid as described in WO2007/121318.

In some embodiments the delivery agent is sodium N-(8-(2-hydroxybenzoyl)amino)caprylate (referred to as "SNAC" herein), also known as sodium 8-(salicyloylamino)octanoate.

Composition

The composition or pharmaceutical composition of the present invention is a solid or dry composition suited for administration by the oral route as described further herein below.

In some embodiments the composition comprises at least one pharmaceutically acceptable excipient. The term "excipient" as used herein broadly refers to any component other than the active therapeutic ingredient(s) or active pharmaceutical ingredient(s) (API(s)). The excipient may be a pharmaceutically inert substance, an inactive substance, and/or a therapeutically or medicinally none active substance.

The excipient may serve various purposes, e.g. as a carrier, vehicle, filler, binder, lubricant, glidant, disintegrant, flow control agent, crystallization inhibitors solubilizer, stabilizer, colouring agent, flavouring agent, surfactant, emulsifier or combinations of thereof and/or to improve administration, and/or absorption of the therapeutically active substance(s) or active pharmaceutical ingredient(s). The amount of each excipient used may vary within ranges conventional in the art. Techniques and excipients which may be used to formulate oral dosage forms are described in Handbook of Pharmaceutical Excipients, 8th edition, Sheskey et al., Eds., American Pharmaceuticals Association and the Pharmaceutical Press, publications department of the Royal Pharmaceutical Society of Great Britain (2017); and Remington: the Science and Practice of Pharmacy, 22nd edition, Remington and Allen, Eds., Pharmaceutical Press (2013).

In some embodiments the excipients may be selected from binders, such as polyvinyl pyrrolidone (povidone), etc.; fillers such as cellulose powder, microcrystalline cellulose, cellulose derivatives like hydroxymethylcellulose, hydroxyethylcellulose, hydroxypropylcellulose and hydroxy-propylmethylcellulose, dibasic calcium phosphate, corn starch, pregelatinized starch, etc.; lubricants and/or glidants such as stearic acid, magnesium stearate, sodium stearylfumarate, glycerol tribehenate, etc.; flow control agents such as colloidal silica, talc, etc.; crystallization inhibitors such as Povidone, etc.; solubilizers such as Pluronic, Povidone, etc.; colouring agents, including dyes and pigments such as iron oxide red or yellow, titanium dioxide, talc, etc.; pH control agents such as citric acid, tartaric acid, fumaric acid, sodium citrate, dibasic calcium phosphate, dibasic sodium phosphate, etc.; surfactants and emulsifiers such as Pluronic, polyethylene glycols, sodium carboxymethyl cellulose, polyethoxylated and hydrogenated castor oil, etc.; and mixtures of two or more of these excipients and/or adjuvants.

The composition may comprise a binder, such as povidone; starches; celluloses and derivatives thereof, such as microcrystalline cellulose, e.g., Avicel PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin. The binder may be selected from the group consisting of dry binders and/or wet granulation binders. Suitable dry binders are, e.g., cellulose powder and microcrystalline cellulose, such as Avicel PH 102 and Avicel PH 200. In some embodiments the composition comprises Avicel, such as Aavicel PH 102. Suitable binders for wet granulation or dry granulation are corn starch, polyvinyl pyrrolidone (povidon), vinylpyrrolidone-vinylacetate copolymer (copovidone) and cellulose derivatives like hydroxymethylcellulose, hydroxyethylcellulose, hydroxypropylcellulose and hydroxyl-propylmethylcellulose. In some embodiments the composition comprises povidone.

In some embodiments the composition comprises a filler which may be selected from lactose, mannitol, erythritol, sucrose, sorbitol, calcium phosphate, such as calciumhydrogen phosphate, microcrystalline cellulose, powdered cellulose, confectioner's sugar, compressible sugar, dextrates, dextrin and dextrose. In some embodiments the composition comprises microcrystalline cellulose, such as Avicel PH 102 or Avicel PH 200.

In some embodiments the composition comprises a lubricant and/or a glidant. In some embodiments the composition comprises a lubricant and/or a glidant, such as talc, magnesium stearate, calcium stearate, zinc stearate, glyceryl behenate, glyceryl debehenate, behenoyl polyoxyl-8 glycerides, polyethylene oxide polymers, sodium lauryl sulfate, magnesium lauryl sulfate, sodium oleate, sodium stearyl fumarate, stearic acid, hydrogenated vegetable oils, silicon dioxide and/or polyethylene glycol etc. In some embodiments the composition comprises magnesium stearate or glyceryl debehenate (such as the product Compritol® 888 ATO).

In some embodiments the composition comprises a disintegrant, such as sodium starch glycolate, polacrilin potassium, sodium starch glycolate, crospovidon, croscarmellose, sodium carboxymethylcellulose or dried corn starch. The composition may comprise one or more surfactants, for example a surfactant, at least one surfactant, or two different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

Hydrotropes

An aspect of the invention relates to a composition comprising a GLP-1 agonist, an absorption enhancer or delivery agent and a hydrotrope. The composition of the present invention further comprises one or more hydrotropes. Hydrotropes like a surfactant includes both a hydrophilic part and a hydrophobic and can form micelles and self-aggregate, however they solubilize solutes without micellar solubilization. The inventors have found that that absorption of the GLP-1 agonist and thus the plasma exposure can be increased by including a hydrotrope in the compositions. Without being bound by theory, it is contemplated that the hydrotrope increases the solubility of the delivery agent, such as a salt of NAC, as exemplified by SNAC herein. As shown by Assay I herein hydrotropes can increase the solubility of SNAC in water.

In one embodiment the hydrotrope is capable of increasing the solubility of SNAC. In one embodiment the hydrotrope is capable of increasing the solubility of a salt of NAC, such as SNAC, at least 2-fold at a concentration of 200 mg/ml at pH 6 at room temperature. In further embodiments, the hydrotrope increases solubility of a salt of NAC, such as SNAC, at least 3-, 4- or 5-fold when measured as described in Assay I herein. In a further embodiment, the hydrotrope increase the solubility of SNAC at least 5-fold, such as 8-fold or such as 10-fold when measured as described in Assay I.

In one embodiment the hydrotrope or hydrotropes are selected from the group consisting of: Nipecotamide, Nicotinamide, p-hydroxybenzoic acid sodium, N,N dimethyl urea, N,N dimethyl benzamide, N,N diethyl nicotinamide, Sodium salicylate, Resorcinol, Sodium benzoate, Sodium Xylenesulfonate, Sodium p-toluenesulfonate, 1-Methylnicotinamide, Pyrogallol, Pyrocathecol, Epigallocatechin gallate, Tannic acid and Gentisic acid sodium salt hydrate.

In one embodiment the hydrotrope or hydrotropes are selected from the group consisting of: Nipecotamide, Nicotinamide, p-hydroxybenzoic acid sodium, N,N dimethyl urea, N,N dimethyl benzamide, N,N diethyl nicotinamide, Sodium salicylate, Resorcinol, Sodium benzoate, Sodium Xylenesulfonate, Sodium p-toluenesulfonate, 1-Methylnicotinamide, Pyrogallol, Pyrocathecol, Epigallocatechin gallate, Tannic acid and Gentisic acid sodium salt hydrate.

In one embodiment the hydrotrope or hydrotropes are selected from the group consisting of: Nicotinamide, p-hydroxybenzoic acid sodium, N,N dimethyl urea, N,N dimethyl benzamide, N,N diethyl nicotinamide, Sodium salicylate, Resorcinol, Sodium benzoate, Sodium Xylenesulfonate, Sodium p-toluenesulfonate, 1-Methylnicotinamide, Pyrogallol, Pyrocathecol, Epigallocatechin gallate and Gentisic acid sodium salt hydrate.

In one embodiment the hydrotrope or hydrotropes are selected from the group consisting of: Nicotinamide, N,N dimethyl benzamide, N,N diethyl nicotinamide, Resorcinol, Sodium benzoate, Sodium Xylenesulfonate, Sodium p-toluenesulfonate, 1-Methylnicotinamide, Pyrogallol, Pyrocathecol and Gentisic acid sodium salt hydrate.

In one embodiment the molecular weight of the hydrotrope is at most 400 g/mol or such as at most 250 g/mol.

In one embodiment the molecular weight of the hydrotrope is at least 80 g/mol or such as at least 100 g/mol In one embodiment the hydrotrope comprises an aromatic ring structure.

In one embodiment the hydrotrope has a similar molecular structure as nicotinamide and Resorcinol, which both comprises an aromatic ring structure. Included herein are also a physiologically acceptable salt thereof, such as the sodium, potassium, chloride or sulphate salt.

In one embodiment the one or more hydrotrope has the structure of Chem I

Chem I:

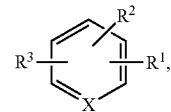

wherein

X is CH or N, $R^1$, $R^2$ and $R^3$ are independently selected from: —H, —OH, —CO$_2$H, —CON(R$^4$)$_2$, —SO$_3$H and —CH$_3$, wherein $R^4$ is —H, —CH$_3$ or —CH$_2$—CH$_3$ or a physiologically acceptable salt thereof.

In one embodiment, where the structure is Chem 1,

X is CH or N, $R^1$ is selected from —OH, —SO$_3$H and CON(R$^4$)$_2$, wherein $R^4$ is —H, —CH$_3$ or —CH$_2$—CH$_3$, R2 is selected from: —OH and —H and R3 is selected from: —H, —OH and —CH$_3$ or a physiologically acceptable salt thereof.

In one embodiment, the hydrotrope has the structure of Chem I, wherein

X is CH,

R1 is is selected from: —OH and —SO$_3$H,

R2 and R3 are independently selected from: —H, —OH and —CH$_3$ or a physiologically acceptable salt thereof.

In one embodiment the one or more hydrotrope has the structure of Chem II
Chem II :

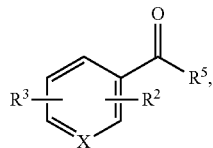

wherein
X is CH or N
R² and R³ are independently selected from: —H, —OH and —CH₃
R⁵ is selected from: —OH and N(R⁴)₂, wherein R4 is —H, —CH₃ or —CH₂—CH₃
or a physiologically acceptable salt thereof.

In a further embodiment, the one or more hydrotrope has the structure of Chem II wherein,
X is CH
R5 is —OH and
R2 and R3 are independently selected from: —OH and —H
or a physiologically acceptable salt thereof.

In a further embodiment, the one or more hydrotrope has the structure of Chem II as defined above, with the proviso that the hydrotrope is not sodium benzoate.

In a further embodiment, the one or more hydrotrope has the structure of Chem II, wherein
X is N,
R⁵ is selected from: —OH and N(R⁴)₂, wherein R4 is —H, —CH₃ or —CH₂—CH₃
R² and R³ are independently selected from: —H, —OH and —CH₃ or
a physiologically acceptable salt thereof.

In a further embodiment, the one or more hydrotrope has the structure of Chem II, wherein
X is N,
R⁵ is NH₂, and
R² and R³ are independently selected from: —H, —OH and —CH₃ or
a physiologically acceptable salt thereof.

In one embodiment the one or more hydrotrope has the structure of Chem III Chem III:

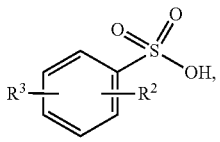

wherein
R² and R³ are independently selected from —H and —CH₃.

In one embodiment the one or more hydrotrope has the structure of Chem IV Chem IV:

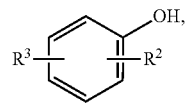

wherein
R2 and R3 are independently selected from: —H and —OH.

In one embodiment the hydrotrope or hydrotropes is/are selected from the group consisting of: Resorcinol, Pyrocatechol, Pyrogallol, Gentisic acid, Xylenesulfonate, p-toluenesulfonate, Nicotinamide, Dimethylbenzamide, Diethylbenzamide, 1-methylnicotinamide, Salicyclic acid, P-Hydroxybenzoic acid and Benzoate.

In one embodiment the hydrotrope or hydrotropes is/are selected from the group consisting of: Resorcinol, Pyrocatechol, Pyrogallol, Gentisic acid, Xylenesulfonate, p-toluenesulfonate, Nicotinamide, Dimethylbenzamide, Diethylbenzamide, 1-methylnicotinamide, Salicyclic acid and P-Hydroxybenzoic acid.

In one embodiment the hydrotrope or hydrotropes is/are selected from the group consisting of: Resorcinol, Pyrocatechol and Pyrogallol, In one embodiment the hydrotrope or hydrotropes is/are selected from the group consisting of: Xylenesulfonate and p-toluenesulfonate In one embodiment the hydrotrope or hydrotropes is/are selected from the group consisting of: Nicotinamide, Dimethylbenzamide, Diethylbenzamide and 1-methylnicotinamide, In one embodiment the hydrotrope or hydrotropes is/are selected from the group consisting of: Gentisic acid, Salicyclic acid, P-Hydroxybenzoic acid and Benzoate.

In one embodiment the hydrotrope or hydrotropes is/are selected from the group consisting of: Gentisic acid, Salicyclic acid and P-Hydroxybenzoic acid.

In one embodiment the hydrotrope or hydrotropes are nicotinamide and/or Resorcinol. In one embodiment the hydrotrope is nicotinamide.

In one embodiment the hydrotrope is not sodium benzoate.

As shown in the examples herein, the composition of the invention comprises a GLP-1 agonist, a delivery agent and a hydrotrope.

The description here below also refers to compositions consisting of specific ingredients, the GLP-1 agonist, the delivery agent and the hydrotrope and optionally a lubricant, the term consisting is to be understood to nevertheless encompass trace amounts of any substance with no effect on the function of the composition. Such substances can be impurities remaining in preparation of the GLP-1 agonist, from the production of the salt of NAC, the hydrotrope preparation or minimal amounts (below 1%) of any pharmaceutical acceptable excipient that do not affect the quality or absorption of the formulation.

In one embodiment the pharmaceutical composition comprises a balanced amount of the hydrotrope relative to the amount of the delivering agent. The effect of the hydrotrope has been observed over a range of concentrations.

In one embodiment the ratio of salt of NAC/hydrotrope (w/w) is at least 0.5, such as at least 0.75 or such as at least 1.

In one embodiment the ratio of salt of NAC/hydrotrope (w/w) is 0.5-10.0 or such as such as 0.5-8 or such as 0.5-5.

In one embodiment the ratio of salt of NAC/hydrotrope (w/w) is 0.5-10.0 or such as 0.75-10.0, 0.5-8.0 or 1-2.0.

In one embodiment the ratio of SNAC/Nicotinamide (w/w) is at least 0.5, such as at least 0.75, such as at least 1.

In one embodiment the ratio of salt of SNAC/Nicotinamide (w/w) is 0.5-10.0 or such as 0.5-8 or such as 0.5-5.

In one embodiment the ratio of salt of SNAC/Nicotinamide (w/w) is 0.5-10.0 or such as 0.75-10.0, 0.5-8.0 or 1-2.0.

In one embodiment the ratio of SNAC/Resorcinol (w/w) is at least 0.5, such as at least 0.75, such as at least 1. In one embodiment the ratio of salt of SNAC/Resorcinol (w/w) is 0.5-10.0 or such as 0.75-10.0, 0.5-8.0 or such as 1-2.0.

In one embodiment the ratio of hydrotrope/salt of NAC (w/w) is at least 0.1, such as at least 0.2 or such as at least 0.3. In one embodiment the ratio of hydrotrope/salt of NAC (w/w) is 0.1-5.0 or such as 0.1-4.0, 0.2-3.0 or 0.25-2.0.

In one embodiment the ratio of Nicotinamide/SNAC/ (w/w) is at least 0.1-5.0 or such as 0.1-4.0, 0.2-3.0 or 0.25-2.0. In one embodiment the ratio of Nicotinamide/SNAC (w/w) is 0.1-5.0 or such as 0.1-4.0, 0.2-3.0 or 0.25-2.0.

In one embodiment the ratio of Resorcinol/SNAC/ (w/w) is at least 0.1-5.0 or such as 0.1-4.0, 0.2-3.0 or 0.25-2.0. In one embodiment the ratio of Resorcinol/SNAC (w/w) is 0.1-5.0 or such as 0.1-4.0, 0.2-3.0 or 0.25-2.0.

Likewise, the amount of lubricant maybe be considered relative to the total amount of the other excipients, here hydrotrope and delivery agent, and not including the GLP-1 agonist. Relatively small amounts of the lubricant are usually included, such as less than 5% of the total weight of the other excipients.

In one embodiment the composition comprises less than 5 w/w % lubricant of the total amount of delivery agent and hydrotrope. In one embodiment the composition comprises 0.25-5%, such as 1-4 w/w % lubricant of the total amount of delivery agent and hydrotrope. In further embodiments the composition comprises 0.25-5%, such as 1-4 w/w % lubricant of the amount of salt of NAC, such as SNAG, and nicotinamide or resorcinol.

The pharmaceutical composition according to the invention is preferably produced in a dosage form suitable for oral administration as described herein below. In the following the absolute amounts of the ingredients of the composition of the invention are provided with reference to the content in a dosage unit i.e. per tablet, capsule or sachet.

The pharmaceutical compositions of the invention may in a further embodiment comprise at most 1000 mg of said salt of N-(8-(2-hydroxybenzoyl)amino)caprylic acid (NAC) per dose unit. In one embodiment the invention relates to a composition wherein a dose unit comprises at most 500 mg of said salt.

In some embodiments the amount of the salt of N-(8-(2-hydroxybenzoyl) amino)caprylic acid per dose unit is at least 0.15 mmol, such as selected from the group consisting of at least 0.20 mmol, at least 0.25 mmol, at least 0.30 mmol, at least 0.35 mmol, at least 0.40 mmol, at least 0.45 mmol, at least 0.50 mmol, at least 0.55 mmol and at least 0.60 mmol.

In some embodiments the amount of the salt of N-(8-(2-hydroxybenzoyl)amino)caprylic acid per dosage unit of the composition is up to 2 mmol, such as up to 1.5 mmol, up to 1 mmol, up to 0.75 mmol, up to 0.6 mmol, up to 0.5 mmol, up to 0.4 mmol, up to 0.3 mmol and up to 0.2 mmol.

In some embodiments the amount of the salt of N-(8-(2-hydroxybenzoyl) amino)caprylic acid per dose unit of the composition is in the range of 0.20-1.5 mmol, 0.25-1.0 mmol 0.30-0.75 mmol or such as 0.45-0.65 mmol.

In some embodiments the amount of SNAC in the composition is at least 50 mg, such as at least 75 mg, at least 100 mg, at least 125 mg, at least 150 mg, at least 175 mg, at least 200 mg, at least 225 mg, at least 250 mg, at least 275 mg and at least 300 mg per dose unit.

In some embodiments the amount of SNAC in the composition is up to 575 mg, such as up to 550 mg, up to 525 mg, up to 500 mg, up to 475 mg, up to 450 mg, up to 425 mg, up to 400 mg, up to 375 mg, up to 350 mg, up to 325 mg per dose unit, or up to 300 mg per dose unit.

In some embodiments the amount of SNAC in the composition is in the range of 75-400 mg, such as from 80-350 mg, such as from around 100 to around 300 mg per dose unit.

In an embodiment, a dose unit of the pharmaceutical compositions of the invention comprises 0.1-100 mg of the GLP-1 agonist.

In some embodiments a dose unit of the composition comprises an amount of GLP-1 agonist is in the range of 0.1-50 mg, 0.2 to 50 mg, 0.5 to 50 mg or 1 to 40 mg.

In some embodiments a dose unit of the composition comprises an amount of GLP-1 agonist is in the range of 0.1-50 mg, 0.1-40 mg, 0.1-30 mg or 0.1-20 mg.

In some embodiments a dose unit comprises 0.5-5 mg of the GLP-1 agonist, such as 0.75-4½ mg, such as 1, 1½, 2, 2½ or 3 mg or 3½, 4, 4½ mg, such as 1-3 or 3-5 mg of the GLP-1 agonist per dose unit.

In some embodiments a dose unit comprises 2 to 20 mg of the GLP-1 agonist, such as 2-15 mg, such as 2, 3, 4 or 5 mg, or such as 8, 10, 12 or 14 mg, such as 15 mg or such as 20 mg of the GLP-1 agonist per dose unit.

In some embodiments a dose unit comprises 5 to 50 mg of the GLP-1 agonist, such as 10-45 mg, such as 20, 30 or 40 mg, or such as 25, 35, or 45 mg, or such as 30-50 mg or such as 20-40 mg of the GLP-1 agonist per dose unit.

As described above the amount of the hydrotrope is to be balanced with the amount of the delivering agents, such as SNAC, but in general a dose unit of the compositions of the invention comprises 10-600 mg of the hydrotrope.

In on embodiment a dose unit comprises 20-400 mg, such as 40-300, such as 50-200 mg, such as 50-175 mg of the hydrotrope.

In on embodiment a dose unit comprises 100-600 mg, such as 100-500, such as 150-400 mg, such as 150-300 mg of the hydrotrope.

In further such embodiments, a unit dose of the composition according to the invention comprises 50-600 mg nicotinamide and/or resorcinol.

In on embodiment a dose unit comprises 50-400 mg, such as 50-300, such as 50-200 mg, such as 50-175 mg nicotinamide and/or resorcinol.

In further such embodiments a unit dose of the composition according to the invention comprises 50-600 mg nicotinamide. In one embodiment a dose unit comprises 50-400 mg, such as 50-300, such as 50-200 mg, such as 50-175 mg nicotinamide.

In one embodiment a unit dose of the composition according to the invention comprises:
i) 0.1-10 mg GLP-1 agonist, such as GLP-1 agonist is Semaglutide, GLP-1 agonist B or GLP-1 agonist C.
ii) 25-600 mg salt of N-(8-(2-hydroxybenzoyl)amino) caprylic acid (NAC), such as the sodium salt of NAC (SNAC) and
iii) 20-600 mg, such as 50-200 mg, nicotinamide or resorcinol and
iv) 0-10 mg lubricant.

In one embodiment a unit dose of the composition according to the invention comprises:
i) 0.1-10 mg GLP-1 agonist, such as GLP-1 agonist is Semaglutide, GLP-1 agonist B or GLP-1 agonist C.
ii) 150-600 mg salt of N-(8-(2-hydroxybenzoyl)amino) caprylic acid (NAC), such as the sodium salt of NAC (SNAG) and
iii) 100-600 mg nicotinamide or resorcinol and
iv) 0-10 mg lubricant.

The amount of GLP-1 agonist may be varied depending on identity of the GLP-1 agonist and the effect desired, i.e. a higher content may be relevant for treating obesity compared to diabetes.

In a preferred embodiment a unit dose of the composition comprises 200-400 mg SNAG, 0.5-10 mg GLP-1 agonist, 100-400 mg hydrotrope and 2-3 mg lubricant.

In a preferred embodiment a unit dose of the composition comprises 200-400 mg SNAC, 1½-10 mg GLP-1 agonist, 100-400 mg hydrotrope and 2-3 mg lubricant.

In a preferred embodiment a unit dose of the composition comprises 200-400 mg SNAC, 5-50 mg GLP-1 agonist, 100-400 mg hydrotrope and 2-3 mg lubricant.

In a preferred embodiment a unit dose of the composition comprises 200-400 mg SNAC, 0.5-10 mg GLP-1 agonist, 100-400 mg nicotinamide and 2-3 mg lubricant.

In a preferred embodiment a unit dose of the composition comprises 200-400 mg SNAC, 1½-10 mg GLP-1 agonist, 100-400 mg nicotinamide and 2-3 mg lubricant.

In a preferred embodiment a unit dose of the composition comprises 200-400 mg SNAC, 5-50 mg GLP-1 agonist, 100-400 mg nicotinamide and 2-3 mg lubricant.

In one embodiment a unit dose of the composition according to the invention comprises:
i) 0.1-10 mg GLP-1 agonist, such as GLP-1 agonist is Semaglutide, GLP-1 agonist B or GLP-1 agonist C.
ii) 25-400 mg salt of N-(8-(2-hydroxybenzoyl)amino) caprylic acid (NAC), such as the sodium salt of NAC (SNAC) and
iii) 20-200 mg nicotinamide or resorcinol and
iv) 0-10 mg lubricant.

The amount of GLP-1 agonist may be varied depending on identity of the GLP-1 agonist and the effect desired, i.e. a higher content may be relevant for treating obesity compared to diabetes.

In a preferred embodiment a unit dose of the composition comprises 80-120 mg SNAC, 0.5-5 mg GLP-1 agonist, 20-200 mg hydrotrope and 1-3 mg lubricant.

In a preferred embodiment a unit dose of the composition comprises 80-120 mg SNAC, 1½-10 mg GLP-1 agonist, 20-200 mg hydrotrope and 1-3 mg lubricant.

In a preferred embodiment a unit dose of the composition comprises 80-120 mg SNAG, 5-50 mg GLP-1 agonist, 20-200 mg hydrotrope and 1-3 mg lubricant.

In a preferred embodiment a unit dose of the composition comprises 80-120 mg SNAC, 0.5-5 mg GLP-1 agonist, 20-200 mg nicotinamide and 1-3 mg lubricant.

In a preferred embodiment a unit dose of the composition comprises 80-120 mg SNAC, 1½-10 mg GLP-1 agonist, 20-200 mg nicotinamide and 1-3 mg lubricant.

In a preferred embodiment a unit dose of the composition comprises 80-120 mg SNAC, 5-50 mg GLP-1 agonist, 20-200 mg nicotinamide and 1-3 mg lubricant.

Dosage Form

The composition may be administered in several dosage forms, for example as a tablet; a coated tablet; a sachet or a capsule such as hard or soft gelatine capsule and all such compositions are considered solid oral dosage forms.

The composition may further be compounded in a drug carrier or drug delivery system, e.g. in order to improve stability and/or solubility or further improve exposure. The composition may be a freeze-dried or spray-dried composition.

The composition may be in the form of a dose unit, such as tablet. In some embodiments the weight of the unit dose is in the range of 50 mg to 1000 mg, such as in the range of 50-750 mg, or such as about 100-500 mg. In some embodiments the weight of the dose unit is in the range of 75 mg to 350 mg, such as in the range of 50-300 mg or 100-400 mg.

In some embodiments the composition may be granulated prior to being compressed to tablets. The composition may comprise a granular part and/or an extra-granular part, wherein the granular part has been granulated and the extra-granular part has been added after granulation.

The granular part may comprise one or more of the GLP-1 agonist, the delivery agent and/or the hydrotrope. In an embodiment the granular part may comprise a further excipient, such as a lubricant and/or glidant. In some embodiments the granular part comprises the delivery agent and the hydrotrope.

In one embodiment the hydrotrope is included in the granular part, the extra-granular part or both.

In some embodiments the granular part comprises magnesium stearate or glyceryl dibehenate.

The GLP-1 agonist may be included in the granular part or the extra-granular part. In some embodiments the extra-granular part comprises the GLP-1 agonist. In an embodiment the extra-granular part may further comprise a lubricant and/or a glidant. In an embodiment the granular part may comprise a lubricant and/or a glidant. In an embodiment the granular part and the extra-granular part comprise a lubricant and/or a glidant.

In some embodiments the lubricant and/or a glidant is magnesium stearate or glyceryl dibehenate.

Preparation of Composition

Preparation of a composition according to the invention may be performed according to methods known in the art.

To prepare a dry blend of tabletting material, the various components are weighed, optionally delumped or sieved and then combined. The mixing of the components may be carried out until a homogeneous blend is obtained.

The term "granules" refers broadly to pharmaceutical ingredients in the form of particles, granules and aggregates which are used in the preparation of solid dose formulations. Generally, granules are obtained by processing a powder or a blend to obtain a solid which is subsequently broken down to obtain granules of the desired size.

If granules are to be used in the tabletting material, granules may be produced in a manner known to a person skilled in the art, for example using wet granulation methods known for the production of "built-up" granules or "broken-down" granules. Methods for the formation of built-up granules may operate continuously and comprise, for example simultaneously spraying the granulation mass with granulation solution and drying, for example in a drum granulator, in pan granulators, on disc granulators, in a fluidized bed, by spray-drying or spray-solidifying, or operate discontinuously, for example in a fluidized bed, in a rotary fluid bed, in a batch mixer, such as a high shear mixer or a low shear mixer, or in a spray-drying drum. Methods for the production of broken-down granules, which may be carried out discontinuously and in which the granulation mass first forms a wet aggregate with the granulation solution, which is subsequently comminuted or by other means formed into granules of the desired size and the granules may then be dried. Suitable equipment for the granulation step are planetary mixers, low shear mixers, high shear mixers, extruders and spheronizers, such as an apparatus from the companies Loedige, Glatt, Diosna, Fielder, Collette, Aeschbach, Alexanderwerk, Ytron, Wyss & Probst, Werner & Pfleiderer, HKD, Loser, Fuji, Nica, Caleva and Gabler. Granules may be also formed by dry granulation techniques in which one or more of the excipient(s) and/or the active pharmaceutical ingredient is compressed to form relatively large moldings, for example slugs or ribbons, which are comminuted by grinding, and the ground material serves as the tabletting material to be later compacted. Suitable equipment for dry granulation is roller compaction equipment from Gerteis, but not limited hereto, such as Gerteis MICRO-PACTOR, MINI-PACTOR and MARCO-PACTOR.

Further methods of obtaining granules can include hot melt extrusion, spray drying, spray granulation and/or ball milling.

In an embodiment the invention relates to a composition comprising
i. a GLP-1 agonist,
ii. a salt of N-(8-(2-hydroxybenzoyl)amino)caprylic acid (NAC) and
iii. a hydrotrope
wherein the composition comprises a granulate of ii) and iii).

In embodiments where the granular part comprises both the delivery agent and the hydrotrope these excipients may be co-processed prior to or in the preparation of the granules.

The granulation maybe be obtained by various methods as described above, wherein ii) and iii) are initially mixed either as powders or by the preparation of a solution comprising both ingredients.

Granules of ii) and iii) may then be obtained by dry granulation of the blend, such as by roller compaction. In an alternative embodiment the blend may be hot melt extruded to obtain an extrudate which is subsequently milled to obtain the granules. This material can then be used directly or in dry granulation/roller compaction process to obtain the final granules.

In one embodiment a solution of ii) and iii) is prepared and subject to spray granulation whereby granules are directly obtained. Alternatively, the solution can be used in a fluid bed spray granulation process. In one embodiment spray drying can be used followed by dry granulation/roller compaction to obtain the granules.

In order to obtain a homogenous product one or more sieving step(s) can be included prior to the final dry granulation step/roller compaction or tablet compression.

To compact the tabletting material into a solid oral dosage form, for example a tablet, a tablet press may be used. In a tablet press, the tabletting material is filled (e.g. force fed or gravity fed) into a die cavity. The tabletting material is then compacted by a set of punches applying pressure. Subsequently, the resulting tablet is ejected from the tablet press. The above mentioned tabletting process is subsequently referred to herein as the "compression process". Suitable tablet presses include, but are not limited to, rotary tablet presses and eccentric tablet presses. Examples of tablet presses include, but are not limited to, the Fette 102i (Fette GmbH), the Korsch XL100, the Korsch PH 106 rotary tablet press (Korsch AG, Germany), the Korsch EK-O eccentric tabletting press (Korsch AG, Germany) and the Manesty F-Press (Manesty Machines Ltd., United Kingdom).

In some embodiments the invention relates to a method of preparation a composition according to the invention. In one embodiment the method of preparing a tablet comprises; a) granulation of a mixture comprising the delivery agent and the hydrotrope b) blending of the granulates of a) with a GLP-1 agonist, and then c) compression of the blend into tablets. The granulation may be a wet or dry granulation. As described above a lubricant such as magnesium stearate or glyceryl behenate may be included in steps a), b) and/or c).

In one embodiment the invention relates to a method for producing a solid pharmaceutical composition comprising the steps of;
i) obtaining a blend comprising a salt of NAC and a hydrotrope,
ii) co-processing the blend of i) and
iii) preparing said solid pharmaceutical composition using the product of ii).

In one embodiment the method is for producing a solid pharmaceutical composition comprising the steps of;
i) obtaining a blend comprising a salt of NAC and a hydrotrope,
ii) heat melt extruding the blend of i) and
iii) preparing said solid pharmaceutical composition, such as tablets, using the extrudate of ii).

The method may as described herein include further steps, such as a step of admixing the extrudate of ii) with an active pharmaceutical ingredient and optionally any further excipients and preparing said solid pharmaceutical composition using the mixture.

Pharmaceutical Indications

The present invention also relates to a composition of the invention for use as a medicament. In particular embodiments the composition of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing 13-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atherosclerosis; mild chronic heart failure; angina pectoris; cardiac bypass reocclusion; intermittent claudication (atherosclerosis obliterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix). In another particular embodiment, the indication is (i). In a further particular embodiment the indication is (v). In a still further particular embodiment the indication is (iix). In some embodiments the indications are type 2 diabetes and/or obesity.

The invention further relates to a method of treatment of an individual in need thereof, comprising administering a therapeutically active amount of a composition according to the present invention to said individual. In a further such embodiments one or more dose units may be administered to said individual in need.

Method of Treatment

The invention further relates to a method of treating a subject in need thereof, comprising administering a therapeutically effective amount of a composition according to the present invention to said subject. In one embodiment the method of treatment is for treatment of diabetes or obesity and/or the further indications specified above.

In some embodiments, a method for treating diabetes is described comprising administering to a subject in need thereof a therapeutically effective amount of a pharmaceutical composition comprising a GLP-1 agonist, a salt of N-(8-(2-hydroxybenzoyl)amino)caprylic acid (NAC), a hydrotrope and optionally, a lubricant.

In some embodiments, a method for treating diabetes is described comprising administering to a subject in need thereof a therapeutically effective amount of a pharmaceutical composition comprising i) 0.1-30 mg GLP-1 agonist, such as GLP-1 agonist is Semaglutide, GLP-1 agonist B or GLP-1 agonist C.

ii) 25-600 mg salt of N-(8-(2-hydroxybenzoyl)amino) caprylic acid (NAC), such as the sodium salt of NAC (SNAG) and iii) 20-600 mg, such as 50-200 mg, nicotinamide or resorcinol and iv) 0-10 mg lubricant.

In some embodiments, the GLP-1 agonist is semaglutide having a formula of N-epsilon26-[2-(2-{2-[2-(2-{2-[(S)-4-carboxy-4-(17-carboxy-heptadecanoylamino)butyrylamino]ethoxy}ethoxy)acetylamino]ethoxy}ethoxy)acetyl] [Aib8, Arg34]GLP-1(7-37) and the salt of N-(8-(2-hydroxybenzoyl)amino)caprylic acid (NAC) is sodium N-(8-(2-hydroxybenzoyl)amino)caprylic acid (SNAC).

In some embodiments, the GLP-1 agonist is $N^{\varepsilon 27}$-[2-[2-[2-[[2-[2-[2-[[(4S)-4-carboxy-4-[10-(4-carboxyphenoxy) decanoylamino]butanoyl]amino] ethoxy]ethoxy]acetyl] amino]ethoxy]ethoxy]-acetyl], $N^{\varepsilon 36}$-[2-[2-[2-[[2-[2-[2-[[(4S)-4-carboxy-4-[10-(4-carboxyphenoxy) decanoylamino]-butanoyl]amino]ethoxy]ethoxy]acetyl] amino]ethoxy]ethoxy]acetyl]-[Aib8,Glu22,Arg26,Lys27, Glu30,Arg34,Lys36]-GLP-1-(7-37)-peptidyl-Glu-Gly (GLP-1 agonist C).

Various examples of a lubricant are described, including magnesium stearate. The composition is administered orally and is in a form of a table, capsule or a sachet.

In a further such embodiments one or more dose units may be administered to said subject in need.

Combination Treatment

The treatment with a composition according to the present invention may also be combined with one or more additional active pharmaceutical ingredient(s), e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, sodium glucose linked transporter 2 (SGLT2) inhibitors; canagliflozin, dapagliflozin, empagliflozin, ertugliflozin, ipragliflozin, tofogliflozin, luseogliflozin, bexagliflozin, remogliflozin etabonate and sotagliflozin, particulally dapagliflozin and empagliflozin, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogues), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonists, mixed Y2/Y4 receptor agonists, MC4 (melanocortin 4) agonists, orexin antagonists, TNF (tumour necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin)

agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogues), gastrin and gastrin analogues.

The invention as described herein is, without limitation hereto further defined by the embodiments described here below and the claims of the document.

EMBODIMENTS

1. A composition comprising
i) a GLP-1 agonist,
ii) a salt of N-(8-(2-hydroxybenzoyl)amino)caprylic acid (NAC) and
iii) a hydrotrope.
2. The composition according to embodiment 1, wherein the hydrotrope is selected from the group of hydrotropes consisting of: Nipecotamide, Nicotinamide, p-hydroxybenzoic acid sodium, N,N dimethyl urea, N,N dimethyl benzamide, N,N diethyl nicotinamide, Sodium salicylate, Resorcinol, Sodium benzoate, Sodium Xylenesulfonate, Sodium p-toluenesulfonate, 1-Methylnicotinamide, Pyrogallol, Pyrocathecol, Epigallocatechin gallate, Tannic acid and Gentisic acid sodium salt hydrate.
3. The composition according to embodiment 1, wherein the hydrotrope is selected from the group of hydrtropes consisting of: Nipecotamide, Nicotinamide, p-hydroxybenzoic acid sodium, N,N dimethyl urea, N,N dimethyl benzamide, N,N diethyl nicotinamide, Sodium salicylate, Resorcinol, Sodium Xylenesulfonate, Sodium p-toluenesulfonate, 1-Methylnicotinamide, Pyrogallol, Pyrocathecol, Epigallocatechin gallate, Tannic acid and Gentisic acid sodium salt hydrate.
4. The composition according to embodiment 1, 2 or 3, wherein the hydrotrope comprises an aromatic ring structure.
5. The composition according to any of the embodiments 1-4, wherein the hydrotrope is not sodium benzoate.
6. The composition according to any of the embodiments 1-5, wherein the hydrotrope has a molecular weight of less than 400 g/mol.
7. The composition according to any of the embodiments 1-6, wherein the hydrotrope has a molecular weight of at least 80 g/mol.
8. The composition according to any of the embodiments 1-7, wherein the hydrotrope increases the solubility of SNAC at least 2-fold.
9. The composition according to any of the embodiments 1-7, wherein the hydrotrope is increases the solubility of SNAC at least 5-fold.
10. The composition according to embodiment 8 or embodiment 9, wherein the solubility is measured at a concentration of 200 mg/ml of the hydrotrope at pH 6.
11. The composition according to embodiment 8, 9 or 10, where in the solubility is measured as room temperature.
12. The composition according to embodiment 8, 9 or 10, where in the solubility is measured as described in Assay I herein.
13. The composition according to embodiment 1, wherein the hydrotrope is Nicotinamide or Resocinol.
14. The composition according to embodiment 1, wherein the hydrotrope is Nicotinamide.
15. The composition according to any of the previous embodiments, wherein the ratio of salt of NAC/hydrotrope (w/w) is at least 0.5.
16. The composition according to any of the previous embodiments, wherein the ratio of salt of NAC/hydrotrope (w/w) is 0.5-10.0 or such as 0.75-10.0, 0.5-8.0 or 1-2.0.
17. The composition according to any of the previous embodiments, wherein the ratio of hydrotrope/salt of NAC (w/w) is at least 0.1.
18. The composition according to any of the previous embodiments, wherein the ratio of hydrotrope/salt of NAC (w/w) is 0.1-5.0 or such as 0.1-4.0, 0.2-3.0 or 0.25-2.0.
19. The composition according to any of the previous embodiments, wherein the composition comprises a lubricant.
20. The composition according to any of the previous embodiments, wherein the composition comprises 0.25-5 w/w % lubricant of the total amount of other excipients.
21. The composition according to any of the previous embodiments, wherein the composition comprises a lubricant selected from magnesium stearate and glyceryl dibehenate.
22. The composition according to any of the previous embodiments, wherein the composition comprises 0.25-5 w/w % magnesium stearate of the total amount of SNAC and nicotinamide.
23. The composition according to any of the previous embodiments, wherein the GLP-1 agonist has T ½ of at least 24 hours in minipigs.
24. The composition according to any of the previous embodiments, wherein the GLP-1 agonist has T ½ of at least 2 hours in rats.
25. The composition according to any of the previous embodiments, wherein the GLP-1 agonist has an EC50 (without HSA) of at most 100 pM, such as at most 50.
26. The composition according to any of the previous embodiments, wherein the GLP-1 agonist has an EC50 (without 1% HSA) of at most 100 pM, such as at most 50.
27. The composition according to any of the previous embodiments, wherein the GLP-1 agonist has a molar mass of at most 50 000 g/mol.
28. The composition according to any of the previous embodiments, wherein the GLP-1 agonist comprises an albumin binding substituent.
29. The composition according to any of the previous embodiments, wherein the GLP-1 agonist comprises a fatty acid or a fatty diacid.
30. The composition according to any of the previous embodiments, wherein the GLP-1 agonist comprises a C16, 018 or C20 fatty acid or a C16, C18 or C20 fatty diacid.
31. The composition according to any of the previous embodiments, wherein the GLP-1 agonist is selected from the group consisting of: liraglutide, semaglutide, GLP-1 agonist B and GLP-1 agonist C.
32. The composition according to any of the previous embodiments, wherein a dose unit comprises 0.1-50 mg of the GLP-1 agonist.
33. The composition according to any of the previous embodiments, wherein the salt of N-(8-(2-hydroxybenzoyl) amino)caprylic acid (NAC) is selected from the group consisting of the sodium salt, potassium salt and/or calcium salt of of N-(8-(2-hydroxybenzoyl)amino)caprylic acid.
34. The composition according to any of the previous embodiments comprising or consisting of:
i) a GLP-1 agonist, such as Semaglutide, GLP-1 agonist B or GLP-1 agonist C.

ii) a salt of N-(8-(2-hydroxybenzoyl)amino)caprylic acid (NAC), such as the sodium salt of NAC (SNAG)
iii) nicotinamide or resorcinol and
iv) a lubricant.

35. The composition according to any of the previous embodiments, wherein a dose unit comprises at most 1000 mg of said salt of N-(8-(2-hydroxybenzoyl)amino)caprylic acid (NAC).

36. The composition according to any of the previous embodiments, wherein a unit dosage comprises
i) 0.1-30 mg, such as 0.1-20 mg GLP-1 agonist, such as Semaglutide, GLP-1 agonist B or GLP-1 agonist C.

ethoxy]acetyl]-[Aib8,Glu22,Arg26,Lys27, Glu30,Arg34, Lys36]-GLP-1-(7-37)-peptidyl-Glu-Gly (GLP-1 agonist C),
ii) 50-600 mg salt of N-(8-(2-hydroxybenzoyl)amino) caprylic acid (NAC), such as the sodium salt of NAC (SNAG) and
iii) 50-200 mg nicotinamide or resorcinol and
iv) 0-10 mg lubricant.

39. The composition according to any of the previous embodiments 1-36, wherein a unit dosage comprises
i) 0.1-30 mg, such as 0.1-20 mg GLP-1 agonist with the following structure

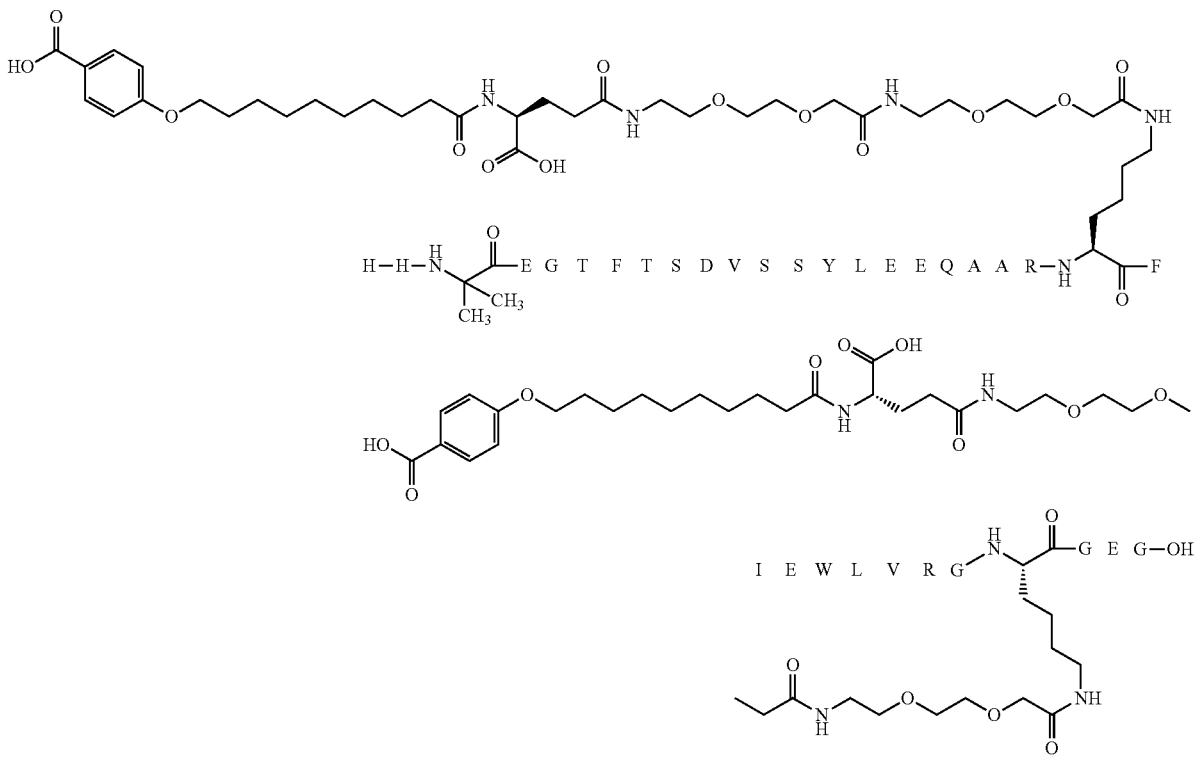

ii) 50-600 mg salt of N-(8-(2-hydroxybenzoyl)amino) caprylic acid (NAC), such as the sodium salt of NAC (SNAC) and
iii) 50-200 mg nicotinamide or resorcinol and
iv) 0-10 mg lubricant.

37. The composition according to any of the previous embodiments, wherein a unit dosage comprises
i) 0.1-30 mg, such as 0.1-20 mg Semaglutide
ii) 50-600 mg salt of N-(8-(2-hydroxybenzoyl)amino) caprylic acid (NAC), such as the sodium salt of NAC (SNAG) and
iii) 50-200 mg nicotinamide or resorcinol and
iv) 0-10 mg lubricant.

38. The composition according to any of the previous embodiments 1-36, wherein a unit dosage comprises
i) 0.1-30 mg, such as 0.1-20 mg $N^{\varepsilon 27}$-[2-[2-[2-[[2-[2-[2-[[(4S)-4-carboxy-4-[10-(4-carboxyphenoxy)decanoylamino]butanoyl]amino] ethoxy]ethoxy]acetyl]amino] ethoxy]ethoxy]-acetyl], $N^{\varepsilon 36}$-[2-[2-[2-[[2-[2-[2-[[(4S)-4-carboxy-4-[10-(4-carboxyphenoxy)decanoylamino]-butanoyl]amino]ethoxy]ethoxy]acetyl]amino]ethoxy]

ii) 50-600 mg salt of N-(8-(2-hydroxybenzoyl)amino) caprylic acid (NAC), such as the sodium salt of NAC (SNAC) and
iii) 50-200 mg nicotinamide or resorcinol and
iv) 0-10 mg lubricant.

40. The composition according to any of the previous embodiments, wherein the composition is a solid composition, such as a solid oral dosage form.

41. The composition according to any of the previous embodiments, wherein the composition comprises a granulate comprising ii).

42. The composition according to any of the previous embodiments, wherein the composition comprises a granulate comprising ii) and iii).

43. The composition according to any of the embodiments 41 and 42, wherein ii) and iii) are co-processed prior to granulation.

44. The composition according to any of the embodiments 41, 42 and 43, wherein the granulate is obtained by hot melt extrusion and milling, spray granulation, wet granulation or dry granulation.

45. The composition according to any of the embodiments 43 or 44, wherein ii) and iii) are blended prior to granulation.

46. The composition according to any of the embodiments 43, 44 or 45, wherein a solution of ii) and iii) is prepared prior to granulation.

47. The composition according to embodiment 46, wherein the granulate is obtained by spray granulation or wet granulation.

48. The composition according to any of the embodiments 46, wherein the solution is spray dried prior to dry granulation.

49. The composition according to embodiment 43, 44 or 45, wherein the granulate is obtained hot melt extrusion and milling.

50. The composition according to embodiment 45, wherein the blend of ii) and iii) is hot melt extruded.

51. The composition according to embodiment 50, wherein the extrudate is milled.

52. The composition according to any of the embodiment 41-51, wherein the granulate is obtained by roller compaction.

53. The composition according to any of the embodiments 46-52, wherein the co-processed ii) and iii) granulate is sieved.

54. The composition according to embodiment 46-53, wherein the milled hot melt extrudate is sieved through a screen of 50-500 µm.

55. The composition according to embodiment 48, wherein the spray dried product is sieved through a screen of 50-500 µm.

56. The composition according to embodiment 41-46, wherein the granulate is obtained by spray granulation.

57. The composition according to embodiment 56, wherein a solution of ii) and iii) is processed by spouted bed or fluid bed spray granulation.

58. The composition according to embodiments 56 and 57, wherein the granulation product is sieved through a 100-500 µm µm screen.

59. The composition according to any of the embodiments 41-58, wherein the composition comprises an extra-granular part.

60. The composition according to any of the embodiments 41-58, wherein the granulate is blended with any further excipients prior to compression.

61. The composition according to any of the embodiments 41-58, wherein the hydrotrope is included in the intra-granular part.

62. The composition according to any of the embodiments 41-58, wherein the GLP-1 agonist is included in an extra granular part.

63. The composition according to any of the embodiments 1-62, wherein the composition is produced by a method comprising the steps of:
a) granulation of a mixture comprising the delivery agent and the hydrotrope
b) blending of the granulates of a) with the GLP-1 agonist, and
c) compressing the blend of b).

64. A composition consisting of:
i) a GLP-1 agonist,
ii) a salt of N-(8-(2-hydroxybenzoyl)amino)caprylic acid (NAC)—
iii) nicotinamide or resorcinol and
iv) optionally a lubricant, such as magnesium stearate.

65. The composition according embodiment 64, wherein the GLP-1 agonist is
Semaglutide, GLP-1 agonist B or GLP-1 agonist C.

66. The composition according embodiment 64, wherein ii) is the sodium salt of NAC (SNAC).

67. The composition according to any of the previous embodiments, wherein the composition is a pharmaceutical composition.

68. The composition according to embodiment 67, wherein the composition is for oral administration.

69. The composition according to embodiment 67, wherein the composition is a solid composition, such as a tablet, a capsule or a sachet for oral administration.

70. The composition according to any of the previous embodiments, wherein the composition is a pharmaceutical composition for use in a method of treating diabetes and/or obesity.

71. A method for producing a solid pharmaceutical composition comprising the steps of;
i) obtaining a blend comprising a salt of NAC and a hydrotrope,
ii) co-processing the blend of i) and
iii) preparing said solid pharmaceutical composition using the product of ii).

72. A method for producing a solid pharmaceutical composition according to embodiment 71, wherein the co-processing if step ii) is performed by
a) heat melt extrusion
b) spray-granulation
c) dry granulation or
d) spray-drying.

73. A method for producing a solid pharmaceutical composition comprising the steps of;
i) obtaining a blend comprising a salt of NAC and a hydrotrope,
ii) heat melt extruding the blend of i)
iii) milling the extrudate of ii) and
iv) preparing said solid pharmaceutical composition using the product of iii).

74. A method for producing a solid pharmaceutical composition comprising the steps of
i) obtaining a blend comprising a salt of NAC and a hydrotrope,
ii) co-processing the blend of i),
iii) admixing the product of ii) with an active pharmaceutical ingredient and optionally any further excipients and
iv) preparing said solid pharmaceutical composition using the mixture of iii).

75. A method for producing a solid pharmaceutical composition comprising the steps of
i) obtaining a blend comprising a salt of NAC and a hydrotrope,
ii) heat melt extruding the blend of i)
iii) milling the extrudate of ii)
iv) admixing the product of ii) with an active pharmaceutical ingredient and optionally any further excipients and
v) preparing said solid pharmaceutical composition using the mixture of iii).

76. A method for producing a composition according to any of the previous embodiments 71-74, wherein the pharmaceutical composition is defined as in any of the previous embodiments 1-70

77. A method for treatment of diabetes or obesity comprising administering to a subject in need a therapeutically effective amount of a composition according to embodiments 1-70 or a composition produced by any of the method of embodiments 71-76.

78. The method according to embodiment 77 wherein said composition is administered, once daily or less frequent.

EXAMPLES

Materials and Methods

Assay I: SNAC Solubility in Combination with Selected Hydrotropes

A series of 18 different hydrotropes were selected for testing. Hydrotropes are weighed off and dissolved in 5 mL ultrapure water (200 mg/mL) and pH was titrated to pH 6 by addition of 2M HCl. Subsequently SNAC (200 mg) is added to the samples and placed on magnetic stirrers (400 rpm). The pH is maintained at pH 6 throughout the experiment by addition of 2M HCl.

After 4 hours of incubation at room temperature the samples were filtered through 0.45 μm syringe filters and the concentration of SNAC in solution is determined using a RP-HPLC method for detection of SNAC. The sample content is calculated based on the peak area of the SNAG peak in the chromatogram relative to the peak area of the SNAC references. Results obtained are presented in table 1, demonstrating that the majority of hydrotropes increase solubility of SNAG significantly.

TABLE 1

Hydrotropic effect of selected hydrotropes (200 mg/mL) on SNAC solubility at pH 6

| Hydrotrope | Replicates (n) | SNAC concentration (mg/mL) | Fold increase in solubility |
| --- | --- | --- | --- |
| SNAC control (no hydrotrope) | 1 | 0.59 | 1 |
| Nipecotamide | 1 | 1.55 | 2.6 |
| Nicotinamide | 5 | 8.63 | 14.6 |
| p-hydroxybenzoic acid sodium | 1 | 1.25 | 2.1 |
| N,N dimethyl urea | 1 | 2.34 | 4.0 |
| N,N dimethyl benzamide | 4 | 22.46 | 38 |
| N,N diethyl nicotinamide | 1 | 4.58 | 7.8 |
| Sodium salicylate | 1 | 1.59 | 2.7 |
| Resorcinol | 6 | 29.95 | 51 |
| Sodium benzoate | 2 | 1.25 | 2.1 |
| Urea | 1 | 0.77 | 1.3 |
| Sodium Xylenesulfonate | 1 | 2.01 | 3.4 |
| Sodium p-toluenesulfonate | 1 | 1.78 | 3.0 |
| 1-Methylnicotinamide | 1 | 2.20 | 3.7 |
| Pyrogallol | 4 | 8.98 | 15 |
| Pyrocatechol | 1 | 23.95 | 40.6 |
| Epigallocatechin gallate | 1 | 5.66 | 9.6 |
| Tannic acid | 1 | 6.31 | 10.7 |
| Gentisic acid sodium salt hydrate | 1 | 2.72 | 4.6 |

Assay II: SNAC Solubility in Varying Concentrations of Nicotinamide and Resorcinol Nicotinamide and resorcinol was weighed off and dissolved in 5 mL ultrapure water to the final concentrations shown in FIGS. 1A & B and pH was titrated to pH 6 by addition of 2M HCl. Subsequently SNAC (200 mg) was added to the samples placed on magnetic stirrers (400 rpm) and pH is maintained at pH 6 throughout the experiment by addition of 2M HCl.

After 4 hours of incubation samples were filtered through 0.45 μm syringe filters and the concentration of SNAC in solution is determined using a RP-HPLC method for detection of SNAC. The sample content is calculated based on the peak area of the SNAC peak in the chromatogram relative to the peak area of the SNAG references. The results are shown in FIG. 1 demonstrating a concentration dependent effect on SNAG solubility of both hydrotropes.

Assay III: Pharmacokinetic Studies in Beagle Dogs

Pharmacokinetic (PK) studies in Beagle dogs are conducted to determine the exposure of the GLP-1 agonists after peroral administration of different dosage forms.

For the pharmacokinetic studies male Beagle dogs are used, 1 to 5 years of age and weighing approximately 10-12 kg at the start of the studies. The dogs are group housed in pens (12 hours light: 12 hours dark), and fed individually and restrictedly once daily with Royal Canin Medium Adult dog (Royal Canin Products, China Branch, or Brogaarden A/S, Denmark). Exercise and group social are permitted daily, whenever possible. The dogs are used for repeated pharmacokinetic studies with a suitable wash-out period between successive dosing's. An appropriate acclimatisation period is given prior to initiation of the first pharmacokinetic study. All handling, dosing and blood sampling of the animals are performed by trained and skilled staff. Before the studies the dogs are fasted overnight and from 0 to 4 h after dosing. Besides, the dogs are restricted to water 1 hour before dosing until 4 hours after dosing, but otherwise have ad libitum access to water during the whole period.

The GLP-1 agonist tablets used for the per oral studies described herein are immediate release SNAC-based tablets dosed orally.

The tablets containing the GLP-1 agonist are administered in the following manner: 10 min prior to tablet administration the dogs are dosed subcutaneously with approximately 3 nmol/kg of SEQ ID NO: 3). The tablets are placed in the back of the mouth of the dog to prevent chewing. The mouth is then closed and 10 mL of tap water is given by a syringe to facilitate swallowing of the tablet. Alternatively, 40 mL of water is administered by gavage just prior to tablet dosing, where after the tablet is dosed and 10 mL of tap water is given by a syringe to facilitate swallowing of the tablet.

Blood Sampling

Blood is sampled at predefined time points for up till 10 hr post dosing to adequately cover the full plasma concentration-time absorption profile of the GLP-1 agonist.

For each blood sampling time point approximately 0.8 mL of whole blood is collected in a 1.5 mL EDTA coated tube, and the tube is gently turned to allowing mixing of the sample with the EDTA. Blood samples (for example 0.8 mL) are collected in EDTA buffer (8 mM) and then centrifuged at 4° C. and 2000 G for 10 minutes. Plasma is pipetted into Micronic tubes on dry ice, and kept at −20° C. until analysis.

Blood samples are taken as appropriate, for example from a venflon in the cephalic vein in the front leg for the first 2 hours and then with syringe from the jugular vein for the rest of the time points (the first few drops are allowed to drain from the venflon to avoid heparin saline from the venflon in the sample).

General Methods for Tablet Preparation

Method 1: Blending for Dry Granulation

Blending is carried out by manual geometric mixing nicotinamide or resorcinol with SNAC followed by blending on a turbula mixer (7 min, 25 rpm). In cases where the magnesium stearate is not included in the initial blending step it was added in a secondary blending step by manual geometric mixing followed by blending on a turbula mixer (2 min, 25 rpm).

Method 2: Dry Granulation

Dry granulation is carried out by roller compaction on a Gerteis MICRO-PACTOR. The roller speed is set at 1 rpm and roller compaction force at 6 kN/cm, fill depth is 8 mm. Subsequent to dry granulation hand sieving of ribbons into granules using an 800 μm wire mesh screen is carried out.

Method 3: Hot Melt Extrusion

Hot melt extrusion is carried out on a Thermo Scientific Process 11 twin screw extruder. SNAC and nicotinamide or resorcinol are blended on a turbula prior to feeding into the extruder (7 min 25 rpm). The equipment is operated at process temperatures varying between 200° C. to 105° C. along the barrel to facilitate the melt extrusion. The screw speed is varied between 50-1000 rpm and material is fed into the extruder using a gravimetric feeder at varying feed rates and extruded through a 2 mm diameter circular die. The resulting extrudates are manually sieved into granules using a final mesh screen between 350 and 149 μm.

Method 4: Spray Drying

Spray drying is carried out on a Büchi B-290 spray drier mounted with a 1.5 mm nozzle (0.7 mm tip and 0.7 mm needle). The equipment is operated at a pump speed between 5-18%, 100% aspirator, 40-42 mm nitrogen pressure and inlet air temperature ranged between 72-120° C. The collected spray dried product is sieved through a 90 screen before further processing by roller compaction (method 2). The spray solution was composed of SNAG and nicotinamide (combined solid content ranging from 93-323 mg/mL).

Method 5: Spray Granulation

Spray granulation is carried out on a Mini-Glatt fluid bed using a top spray configuration (0.5 mm nozzle, 0.35 bar nozzle air pressure) with satisfactory fluidisation air pressure and 40-50° C. process inlet air temperature. In the initial batch process no solid charge is used and the resulting product is collected and sieved through a 355 μm screen. A secondary spray granulation batch process is carried out using the material collected from the initial batch process as starting material and a post process drying in the equipment is carried out. The final material was sieved through a <500 μm screen. The spray solution was composed of SNAC and nicotinamide (combined solid content 500 mg/mL).

Method 6: Ball Milling

Ball milling is carried out either on a Fritsch pulverisette 6 planetary ball mill using a 250 mL zirconium oxide bowl and 55 (10 mm) agate grinding balls for up to 3 hours at 300 rpm. Cryo ball milling is carried out on a Retsch MM200 ball mill with 10 mL stainless steel vessels and a single 20 mm stainless steel ball. The filled sample chamber is submerged in liquid nitrogen until the nitrogen stops boiling and subsequently milled for 15 min at 20 1/s, this process was repeated four times. For both milling methods the collected product is sieved through a 90 μm screen before further processing.

Method 7: Blending for Tablet Compression

Blending is carried out by manual geometric mixing the intermediate granulate with GLP-1 agonist followed by blending on a turbula mixer (7 min, 25 rpm). In compositions including magnesium stearate or glyceryl dibehenate it was sieved through a 125 μm or 355 μm mesh and added in a secondary blending step by manual geometric mixing followed by blending on a turbula mixer (2 min, 25 rpm).

Method 8: Tablet Preparation

Tablets are produced on a Kilian Style One or a Fette 1021 mounted with a single set of punches, resulting in 6.5 mm×11 mm, 7.2 mm×12 mm or 8.5 mm×16 mm oval compound cup tablets having no score. Punch size is chose according to the total tablet weight. For the Kilian Style One the press speed is set to 10% and for Fette 102i the press speed is set at 20 rpm. The fill volume is adjusted to obtain tablets having target weights based on composition. Compression forces around 3 to 25 kN are applied to obtain tablets with a crushing strength of around 20-120 N respective to the tablet size.

Example 1—Preparation of Compositions

Tablets with different amounts of GLP-1 agonist, SNAC and further excipients were prepared. The content of the prepared compositions is provided in Table 1 (Table 1.1, Table 1.2 and Table 1.3). GLP-1 agonist A is semaglutide, GLP-1 agonist B is Diacylated [Aib8,Arg34,Lys37]GLP-1 (7-37) (Example 2 of WO2011/080103) and GLP-1 agonist C is Diacylated-[Aib8,Glu22,Arg26,Lys27,Glu30,Arg34,Lys36]-GLP-1-(7-37)-peptidyl-Glu-Gly (Example 31 of WO2012/140117). Semaglutide can be prepared according to the method described in WO2006/097537, Example 4. GLP-1 agonists B and C can be prepared as described in WO2011/080103 and WO2012/140117, respectively. SNAG was prepared according to the method described in WO2008/028859.

Reference compositions A, B and C were generally prepared as described in WO2013/139694. The test compositions (A1, A2 and B2-B4, were generally prepared as described in method 1 and 2 above, with minor variations in the process prior to roller compaction and tablet preparation as specified below.

Example 2—Solid compositions

Tablets with different amounts of GLP-1 agonist, SNAG and further excipients were prepared. The content of the prepared compositions is provided in Table 3 (Table 3.1 and Table 3.2).

Reference compositions A, B and C were generally prepared as described in

The test composition B14 was prepared as described in method 5, 7 and 8 above. The test compositions B11-13 and A3 were prepared as described in method 2, 4, 7 and 8 above.

The test compositions B1, B6-10, A1-2, and C1-C4 were generally prepared as described in method 3, 7 and 8 above, with minor variations in the process as specified below. Composition B1 was not sieved post extrusion; instead the extrudates were submerged in liquid nitrogen and reduced in particle size using a mortar and pestle. GLP-1 derivative was added into the mortar and co-ground to prepare the blend that was compressed into tablets.

The test compositions B5 and B17 were generally prepared as described in method 1, 2, 7 and 8 above, with minor variations in the process as specified below. SNAG (without resorcinol or nicotinamide) was blended on a turbula mixer with 79.4% of the total magnesium stearate (30 min, 25 rpm) and roller compacted according to method 2. Fines (<90 μm) were removed from the resulting granulate by sieving. In composition B5 resorcinol was sieved through a 350 pm mesh prior to blending in method 7. In composition B17 nicotinamide was sieved through a 315 μm mesh prior to blending in method 7.

The test compositions B15-16 were generally prepared as described in method 2, 6, 7 and 8 above, with minor variations in the as process as specified below. To prepare test compositions B15-16 the following procedure was followed; SNAG and nicotinamide were mixed by manual geometric mixing followed by blending on a turbula mixer (7 min, 25 rpm). The resulting blends were milled according to method 6 (B15 ball milled & B16 cryo ball milled) followed by roller compaction as described in method 1. The obtained granulates were further processed into tablets according to method 7 and 8.

The test compositions B2-4 and B18-19 were generally prepared as described in method 1, 2, 7, and 8 above, with minor variations in the process as specified below. To prepare test compositions B2-4 and B18-19 the following procedure was followed; magnesium stearate was passed through a 355 μm or finer sieve. SNAG and nicotinamide (B18-B19) or resorcinol (B2-B4) were sieved <53 μm and the correct amounts of excipients was weighed off. The excipients were blended according to method 1 with the following variations. In composition B2 magnesium stearate was added in the secondary blending step (62.5% of the composition, remainder was added in method 7. In composition B3 magnesium stearate was added in the secondary blending step. In composition B18 62.5% of the total magnesium stearate was included (remainder was added in method 7) and blending time on the turbula mixer was increased to 15 min. These blends were then roller compacted according to method 2 followed by preparation of the final tablets according to method 7 and 8.

TABLE 3.1

Overview of compositions with GLP-1 agonist B

| Composition | GLP-1 agonist A (mg) | SNAC (mg) | Resorcinol (mg) | Nicotinamide (mg) | Magnesium stearate (mg) | Glyceryldibehenate (mg) | Povidone (mg) | MCC (mg) |
|---|---|---|---|---|---|---|---|---|
| B | 5 | 300 | — | — | 9.7 | — | 8 | 80 |
| B1 | 5 | 100 | 67 | — | 0 | — | — | — |
| B2 | 5 | 100 | 180 | — | 4.5 | — | — | — |
| B3 | 5 | 100 | 61 | — | 2.5 | — | — | — |
| B4 | 5 | 300 | 180 | — | — | 2.2 | — | — |
| B5 | 5 | 300 | 180 | — | 9.7 | — | — | — |
| B6 | 5 | 273 | — | 168 | — | 2.2 | — | — |
| B7 | 5 | 100 | — | 61 | — | 0.8 | — | — |
| B8 | 5 | 353 | — | 88 | — | 2.2 | — | — |
| B9 | 5 | 100 | — | 150 | 1.3 | — | — | — |
| B10 | 5 | 100 | — | 100 | 1 | — | — | — |
| B11 | 5 | 273 | — | 168 | — | 2.2 | — | — |
| B12 | 5 | 100 | — | 180 | 3.2 | — | — | — |
| B13 | 5 | 100 | — | 60 | 1.6 | — | — | — |
| B14 | 5 | 100 | — | 67 | 0.8 | — | — | — |
| B15 | 5 | 100 | — | 67 | — | — | — | — |
| B16 | 5 | 100 | — | 67 | — | — | — | — |
| B17 | 5 | 300 | — | 540 | 9.7 | — | — | — |
| B18 | 5 | 100 | — | 180 | 4.5 | — | — | — |
| B19 | 5 | 273 | — | 168 | — | 2.2 | — | — |

TABLE 3.2

Overview of compositions with GLP-1 agonist A

| Composition | GLP-1 agonist B(mg) | SNAC (mg) | Nicotinamide (mg) | Magnesium stearate (mg) | Glyceryl dibehenate (mg) | Povidone (mg) | MCC (mg) |
|---|---|---|---|---|---|---|---|
| A | 3 | 300 | — | 9.7 | — | 8 | 80 |
| A1 | 3 | 273 | 168 | — | 2.2 | — | — |
| A2 | 3 | 100 | 67 | 0.8 | — | — | — |
| A3 | 3 | 100 | 67 | 1.7 | — | — | — |

TABLE 3.3

Overview of compositions with GLP-1 agonist C

| Composition | GLP-1 agonist C (mg) | SNAC (mg) | Nicotinamide (mg) | Magnesium stearate (mg) | Povidone (mg) | MCC (mg) |
|---|---|---|---|---|---|---|
| C | 4 | 300 | — | 9.7 | 8 | 80 |
| C1 | 4 | 100 | 67 | 0.8 | — | — |
| C2 | 4 | 274 | 182 | 2.4 | — | — |
| C3 | 4 | 200 | 133 | 1.6 | — | — |
| C4 | 4 | 100 | 25 | 0.8 | — | — |

The exposure of the GLP-1 agonists was evaluated in a pharmacokinetic study as described in Assay III demonstrating several folds increase (Table 4) in the dose corrected plasma concentrations of the compositions comprising Resorcinol or Nicotinamide.

TABLE 4.1

Overview of compositions with GLP-1 agonist B

| GLP-1 agonist | Formulation composition | replicates (n) | Dose corrected AUC 0-30 min (hr*kg/L) * 100) | Dose corrected exposure t = 30 min (kg/L) |
|---|---|---|---|---|
| B | Reference B | 24 | 3.16 | 0.17 |
| B | B1 | 16 | 13.38 | 0.50 |
| B | B2 | 16 | 10.06 | 0.42 |
| B | B3 | 16 | 14.86 | 0.61 |
| B | B4 | 16 | 14.99 | 0.64 |
| B | B5 | 8 | 9.98 | 0.44 |
| B | B6 | 16 | 13.5 | 0.66 |
| B | B7 | 16 | 15.99 | 0.72 |
| B | B8 | 16 | 8.35 | 0.45 |
| B | B9 | 16 | 13.2 | 0.55 |
| B | B10 | 14 | 10.10 | 0.40 |
| B | B11 | 16 | 12.16 | 0.62 |
| B | B12 | 16 | 11.26 | 0.46 |
| B | B13 | 15 | 11.85 | 0.49 |
| B | B14 | 16 | 12.64 | 0.53 |
| B | B15 | 15 | 12.76 | 0.39 |
| B | B16 | 14 | 10.06 | 0.39 |
| B | B17 | 15 | 8.10 | 0.45 |
| B | B18 | 16 | 10.37 | 0.48 |
| B | B19 | 11 | 8.69 | 0.40 |

TABLE 4.2

Overview of compositions with GLP-1 agonist A

| GLP-1 agonist | Formulation composition | replicates (n) | Dose corrected AUC 0-30 min ((hr*kg/L)* 100) | Dose corrected exposure t = 30 min (kg/L) |
|---|---|---|---|---|
| A | Reference A | 23 | 1.68 | 0.10 |
| A | A1 | 16 | 5.99 | 0.33 |
| A | A2 | 32 | 4.61 | 0.22 |
| A | A3 | 32 | 4.38 | 0.19 |

TABLE 4.3

Overview of compositions with GLP-1 agonist C

| GLP-1 agonist | Formulation composition | replicates (n) | Dose corrected AUC 0-30 min (hr*kg/L) * 100) | Dose corrected exposure t = 30 min (kg/L) |
|---|---|---|---|---|
| C | C | 64 | 4.05 | 0.23 |
| C | C1 | 48 | 12.59 | 0.49 |
| C | C2 | 31 | 13.42 | 0.63 |
| C | C3 | 16 | 11.45 | 0.54 |
| C | C4 | 16 | 12.15 | 0.49 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A composition comprising
   i) semaglutide,
   ii) sodium salt of N-(8-(2-hydroxybenzoyl)amino) caprylic acid (SNAC), and
   iii) nicotinamide, wherein the nicotinamide increases the solubility of SNAC at least 5-fold when the solubility is measured at a concentration of 200 mg/ml of the nicotinamide at a pH of 6.

2. The composition according to claim 1, wherein the ratio of the SNAC/nicotinamide (w/w) (w/w) is 0.5-10.

3. The composition according to claim 2, wherein the ratio of the SNAC/nicotinamide (w/w) is 0.5-8.

4. The composition according to claim 3, wherein the ratio of the SNAC/nicotinamide (w/w) is 0.5-5.

5. The composition according to claim 4, wherein the composition further comprises a lubricant selected from the group consisting of magnesium stearate and glyceryl dibehenate.

6. The composition according to claim 3, wherein the composition further comprises a lubricant selected from the group consisting of magnesium stearate and glyceryl dibehenate.

7. The composition according to claim 1, wherein the composition further comprises a lubricant.

8. The composition according to claim 7, wherein a unit dosage is:
   i) 0.1-30 mg of the semaglutide,
   ii) 50-600 mg of the SNAC,
   iii) 20-200 mg of the nicotinamide, and
   iv) 0-10 mg of the lubricant.

9. The composition according to claim 8, wherein the lubricant is selected from the group consisting of magnesium stearate and glyceryl dibehenate.

10. The composition according to claim 7, wherein the lubricant is selected from the group consisting of magnesium stearate and glyceryl dibehenate.

11. The composition according to claim 1, wherein the composition is a solid composition.

12. The composition according to claim 1 wherein the composition is a pharmaceutical composition suitable for oral administration.

* * * * *

SEQUENCE LISTING

<160> NUMBER OF SEQ ID NOS: 6

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 40

```
<212> TYPE: PRT
<213> ORGANISM: Heloderma suspectum

<400> SEQUENCE: 2

His Gly Glu Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
        35                  40

<210> SEQ ID NO 3
<211> LENGTH: 29
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 4
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: This amino acid residue is covalently attached
      to a substituent

<400> SEQUENCE: 4

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: The amino acid residue is modified with a
      subsitutent
<220> FEATURE:
<221> NAME/KEY: MOD_RES
<222> LOCATION: (31)..(31)
<223> OTHER INFORMATION: The amino acid residue is modified with a
      subsitutent

<400> SEQUENCE: 5

His Xaa Glu Gly Thr Phe Thr Ser Asp Val Ser Ser Tyr Leu Glu Gly
1               5                   10                  15
```

```
Gln Ala Ala Lys Glu Phe Ile Ala Trp Leu Val Arg Gly Arg Lys
            20                  25                  30

<210> SEQ ID NO 6
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (21)..(21)
<223> OTHER INFORMATION: The amino acid residue is modified with a
      substituent
<220> FEATURE:
<221> NAME/KEY: MOD_RES
<222> LOCATION: (30)..(30)
<223> OTHER INFORMATION: The amino acid residue is modified with a
      substituent

<400> SEQUENCE: 6

His Xaa Glu Gly Thr Phe Thr Ser Asp Val Ser Ser Tyr Leu Glu Glu
1               5                   10                  15

Gln Ala Ala Arg Lys Phe Ile Gly Trp Leu Val Arg Gly Lys Gly Glu
            20                  25                  30

Gly
```